United States Patent [19]

Miller, III et al.

[11] Patent Number: 6,010,901
[45] Date of Patent: Jan. 4, 2000

[54] SALMONELLA VIRULENCE GENES

[75] Inventors: Samuel I. Miller, III, Brookline; John J. Mekalanos, Cambridge, both of Mass.

[73] Assignees: The General Hospital Corporation, Boston; President and Fellows of Harvard College, Cambridge, both of Mass.

[21] Appl. No.: 08/475,749

[22] Filed: Jun. 7, 1995

Related U.S. Application Data

[60] Division of application No. 08/090,526, Jul. 9, 1993, Pat. No. 5,599,537, which is a continuation-in-part of application No. 07/629,602, Dec. 18, 1990, abandoned.

[51] Int. Cl.$^7$ ............................ C12N 15/74; C07H 21/04
[52] U.S. Cl. ........................................ 435/320.1; 536/23.7
[58] Field of Search ............................. 424/93.2, 200.1; 435/172.1, 172.3, 252.3, 252.8, 320.1; 536/23.7

[56] References Cited

U.S. PATENT DOCUMENTS

| 4,837,151 | 6/1989 | Stocker | 424/200.1 |
| 4,888,170 | 12/1989 | Curtiss, III | 424/93 |

FOREIGN PATENT DOCUMENTS

| WO 88/09669 | 12/1988 | WIPO . |
| WO 90/11687 | 10/1990 | WIPO . |
| WO A 92/11361 | 7/1992 | WIPO . |
| WO 92/17785 | 10/1992 | WIPO . |

OTHER PUBLICATIONS

Abshire et al., "Analysis of Proteins Synthesized by *Salmonella typhimurium* during Growth within a Host Macrophage", *J. Bacteriol.*, 175:3734–43 (1993).
Crosa et al., "Molecular Relationships Among the Salmonelleae," *J. of Bacteriology*, 115(1):307–315.
Groisman et al., "*Salmonella typhimurium* phoP virulence gene is a transcriptional regulator," *Proc. Natl. Acad. Sci. USA*, 86:7077–7081 (1989).
Miller et al., "Salamonella Vaccines With Mutations in The PhoP Virulence Regulon," *Institut Pasteur/Elsevier* 141:817–821 (1990).
Pulkkinen et al., "A *Salmonella typhimurium* Virulence Protein Is Similar to a *Yersinia enterocolitica* Invasion Protein and a Bacteriophage Lamda Outer Membrane Protein," *J. of Bacteriology* 173(1) =86–93, 1991.
Arico et al., Proc. Natl. Acad. Sci., 86:6671–75, 1989.
Miller et al., Annals of the New York Academy of Sciences, 569:145–154, 1989.
Stock et al., Microbiological Reviews, 53:450–90, 1989.
Hoiseth et al., Nature, 291:238–239, 1981.
Bernardini et al., Jour. of Bact., 172:6274–6281, 1990.
Leroux et al., The EMBO Journal, 6:849–856, 1987.
Curtis et al., Immunobiology of Proteins and Peptides V Vaccines, M.Z. Atassi, ed., pp. 33–47, 1989.
Miller et al., Proc. Natl. Acad. Sci. USA 86:5054–5058, 1989.
Curtis et al., Current Topics in Microbiology and Immunology, 146:35–49, 1989.
Curtiss, Biotech, 8:237–240, 1990.
Galan et al., Microbial Pathogenesis, 6:433–43, 1989.
Curtiss et al., Immunological Investigations, 18:583–596, 1989.
Kier et al., Jour of Bacteriology, 138:155–61, 1979.
Curtiss et al., Infection and Immunity, 55:3035–43, 1987.
Fields et al., Science, 243:1059–1062, 1989.
Galan, Abstracts of 89th Annual Meeting of the American Society for Microbiology, E–9, 1989.
Miller et al., Journal of Bacteriology, 170:2575–2583, 1988.
Taylor et al., Journal of Bacteriology, 171:1870–1878, 1989.
Kier et al., Journal of Bacteriology, 130:399–410, 1977.
Michaelis et al., Journal of Bacteriology, 154:366–374, 1983.
Kukral et al., Journal of Bacteriology, 169:1787–1793, 1987.
Mekalanos, Cell, 35:253–262, 1983.
Beattie et al., Journal of Bacteriology, 172:6997–7004, 1990.
Foster et al., Journal of Bacteriology, 172:771–778, 1990.
Lee et al., Proc. Natl. Acad. Sci. USA, 87:4304–4308, 1990.
Lee et al., Proc. Natl. Acad. Sci. USA, 89:1847–1851, 1992.
Miller et al., Journal of Bacteriology, 172:2485–2490, 1990.
Aranda et al., Proc. Natl Acad. Sci. USA 89:10079–10083, 1992.
Stone et al., Journal of Bacteriology, 174:3945–3952, 1992.
Miller et al., Infection and Immunity, 60:3763–3770, 1992.
Galan et al., Infection and Immunity, 59:2901–2908, 1991.
Sanderson et al., Microbiological Reviews, 52:485–532, 1988.
Miller et al., "Salmonella Vaccines With Mutations in the phoP Virulence Regulon", *Res. Microbiol.*, 141:817–821 (1990).
Miller et al., "the PhoP virulence regulon and live oral Salmonella vaccines", *Vaccine*, 11(2):122–125 (1993).
Miller et al., "PhoP/PhoQ: macrophage–specific modulators of Salmonella virulence?", *Molecular Microbiology 5(9)*:2073–2078 (1991).
Dougan et al. (1988) Construction and characterization of vaccine strains of Salmonella harboring mutations in two different aro genes. J. Infect. Dis. 158:1329–1335, Dec. 1988.
Miller et al. (1990) Characterization of defensin resistance phenotypes associated with mutations in the phoP virulence regulon of *Salmonella typhimurium*. Infection Immunity 58:3706–3710, Nov. 1990.
O'Callaghan et al. (1988) Characterization of aromamtic–and purine–dependent *Salmonella typhimurium*: attenuation, persistence, and ability to induce protective immunity in BALB/c mice. Infection Immunity 56:419–423, Feb. 1988.

*Primary Examiner*—George C. Elliott
*Assistant Examiner*—Robert Schwartzman
*Attorney, Agent, or Firm*—Fish & Richardson P.C.

[57] ABSTRACT

A vector capable of integrating into the chromosome of Salmonella including a first DNA sequence encoding a heterologous protein, a second DNA sequence encoding a marker, and a third DNA sequence encoding a phoP regulatory region regulated gene product necessary for virulence, the third DNA sequence being mutationally inactivated.

25 Claims, 4 Drawing Sheets

```
GTTAACCACT CTTAATAATA ATGGGTTTTA TAGCGAAATA CACTTTTTTA TCGCGTGTTC    60
AATATTTGCG TTAGTTATTA TTTTTTTGGA ATGTAAATTC TCTCTAAACA CAGGTGATAT   120
TTATCTTGGA ATTGTGGTGT TGATTCTATT CTTATAATAT AACAAGAAAT GTTGTAACTG   180
                                            *
ATAGATATAT TAAAAGATTA AATCGGAGGG GGAATAAAGC GTGCTAAGCA TCATCGTGAA   240
TATGATTACA GCGCCTGCGA TGGCATATAA CCGTATTGCG GATGGAGCGT CACGTGAGGA   300
CTGTGAAGCA CAATGCGATA TGTTCTGATT ATATGGCGAG TTTGCTTAAT GACATGTTTT   360
TAGCCGAACG GTGTCAAGTT TCTTAATGTG GTTGTGAGAT TTTCTCTTTA AATATCAAAA   420
TGTTGCATGG GTGATTTGTT GTTCTATAGT GGCTAAAGAC TTTATGGTTT CTGTTAAATA   480
TATATGCGTG AGAAAAATTA GCATTCAAAT CTATAAAAGT TAGATGACAT TGTAGAACCG   540
GTTACCTAAA TGAGCGATAG AGTGCTTCGG TAGTAAAAAT ATCTTTCAGG AAGTAAACAC   600
ATCAGGAGCG ATAGCGGTGA ATTATTCGTG GTTTTGTCGA TTCGGCATAG TGGCGATAAC   660
TGAATGCCGG ATCGGTACTG CAGGTGTTTA AACACACCGT AAATAATAAG TAGTATTAAG   720
                                                                  728
GAGTTGTT
                                                                  776
ATG AAA AAT ATT ATT TTA TCC ACT TTA GTT ATT ACT ACA AGC GTT TTG
Met Lys Asn Ile Ile Leu Ser Thr Leu Val Ile Thr Thr Ser Val Leu
                 5              10              15
                                                                  824
GTT GTA AAT GTT GCA CAG GCC GAT ACT AAC GCC TTT TCC GTG GGG TAT
Val Val Asn Val Ala Gln Ala Asp Thr Asn Ala Phe Ser Val Gly Tyr
            20              25              30
                                                                  872
GCA CGG TAT GCA CAA AGT AAA GTT CAG GAT TTC AAA AAT ATC CGA GGG
Ala Arg Tyr Ala Gln Ser Lys Val Gln Asp Phe Lys Asn Ile Arg Gly
        35              40              45
                                                                  920
GTA AAT GTG AAA TAC CGT TAT GAG GAT GAC TCT CCG GTA AGT TTT ATT
Val Asn Val Lys Tyr Arg Tyr Glu Asp Asp Ser Pro Val Ser Phe Ile
        50              55              60
                                                                  968
TCC TCG CTA AGT TAC TTA TAT GGA GAC AGA CAG GCT TCC GGG TCT GTT
Ser Ser Leu Ser Tyr Leu Tyr Gly Asp Arg Gln Ala Ser Gly Ser Val
65          70              75              80
                                                                 1016
GAG CCT GAA GGT ATT CAT TAC CAT GAC AAG TTT GAG GTG AAG TAC GGT
Glu Pro Glu Gly Ile His Tyr His Asp Lys Phe Glu Val Lys Try Gly
                85              90              95
                                                                 1064
TCT TTA ATG GTT GGG CCA GCC TAT CGA TTG TCT GAC AAT TTT TCG TTA
Ser Leu Met Val Gly Pro Ala Tyr Arg Leu Ser Asp Asn Phe Ser Leu
            100             105             110
                                                                 1112
TAC GCG CTG GCG GGT GTC GGC ACG GTA AAG GCG ACA TTT AAA GAA CAT
Tyr Ala Leu Ala Gly Val Gly Thr Val Lys Ala Thr Phe Lys Glu His
        115             120             125
                                                                 1160
TCC ACT CAG GAT GGC GAT TCT TTT TCT AAC AAA ATT TCC TCA AGG AAA
Ser Thr Gln Asp Gly Asp Ser Phe Ser Asn Lys Ile Ser Ser Arg Lys
130             135                     140
```

FIG. 3A

```
ACG GGA TTT GCC TGG GGC GCG GGT GTA CAG ATG AAT CCG CTG GAG AAT    1208
Thr Gly Phe Ala Trp Gly Ala Gly Val Gln Met Asn Pro Leu Glu Asn
145             150                 155                 160

ATC GTC GTC GAT GTT GGG TAT GAA GGA AGC AAC ATC TCC TCT ACA AAA    1256
Ile Val Val Asp Val Gly Tyr Glu Gly Ser Asn Ile Ser Ser Thr Lys
                165                 170                 175

ATA AAC GGC TTC AAC GTC GGG GTT GGA TAC CGT TTC TGA AAAGC          1300
Ile Asn Gly Phe Asn Val Gly Val Gly Tyr Arg Phe (SEQ ID NO: 5)
        180                 185

ATAAGCTATG CGGAAGGTTC GCCTTCCGCA CCGCCAGTCA ATAAAACAGG GCTTCTTTAC   1360
CAGTGACACG TACCTGCCTG TCTTTTCTCT CTTCGTCATA CTCTCTTCGT CATAGTGACG   1420
CTGTACATAA CATCTCACTA GCATAAGCAC AGATAAAGGA TTGTGGTAAG CAATCAAGGT   1480
TGCTCAGGTA GGTGATAAGC AGGAAGGAAA ATCTGGTGTA ATAACGCCA GATCTCACAA    1540
GATTCACTCT GAAAAATTTT CCTGGAATTA ATCACAATGT CATCAAGATT TTGTGACCGC   1600
CTTCGCATAT TGTACCTGCC GCTGAACGAC TACTGAAAAG TAGCAAGGTA TGTATTTTAT   1660
CCAGGAGAGC ACCTTTTTTG CGCCTGGCAG AAGTCCCCAG CCGCCACTAG CTCAGCTGGA   1720
TAGAGCATCA ACCTCCTAAG TTGATGGTGC GAGGTTCGAG GCCTCGGTGG CGGTCCAATG   1780
TGGTTATCGT ATAATGTTAT TACCTCAGTG TCAGGCTGAT GATGTGGGTT CGACTCCCAC   1840
TGACCACTTC AGTTTTGAAT AAGTATTGTC TCGCAACCCT GTTACAGAAT AATTTCATTT   1900
ATTACGTGAC AAGATAGTCA TTTATAAAAA ATGCACAAAA ATGTTATTGT CTTTTATTAC   1960
TTGTGAGTTG TAGATTTTTC TTATGCGGTG AATCCCCCTT TGCGGCGGGG CGTCCAGTCA   2020
AATAGTTAAT GTTCCTCGCG AACCATATTG ACTGTGGTAT GGTTCACCGG GAGGCACCCG   2080
GCACCGCAAT TTTTTATAAA ATGAAATTCA CACCCTATGG TTCAGAGCGG TGTCTTTTTA   2140
CATCAGGTGG GCAAGCATAA TGCAGGTTAA CTTGAAAGAT ACGATCAATA GCAGAAACCA   2200
GTGATTTCGT TTATGGCCTG GGGATTTAAC CGCGCCAGAG CGTATGCAAG ACCCTGGCGC   2260
GGTTGGCCGG TGATCGTTCA ATAGTGCGAA TATGAATGGT TACCAGCCGC CTGCGAATTC   2320
```

(SEQUENCE ID NO. 1)    FIG. 3B

```
5'    GAG  CGC  ATT  ATC  AGA  TAA  ATT  GAT  TTA  TTTCTCACT
TTC   ATT  CTA  TTT  TCA       TCA
GGA   ATC  CCT  GTG  TCC  TGT  GCG  GTA  ATC  TGC  TGCTATCGA
GAA   CGA  CAG  ACA  TCG
CTA   ACA  GTA  TAT  ATG  GAA  ACA  TCA  AAA  GAG  AAGACGATA
ACA   AGC  CCA  GGG  CCA  TAC
ATA   GTT  CGA  TTA  CTT  AAC  AGC  TCA  CTG  AAC  GGCTGTGAG
TTT   CCA  TTG  CTG  ACA  GGC
CGA   ACA  CTC  TTT  GTG  GTA  GGT  CAG  AGT  GAT  GCGCTCACT
GCT   TCA  GGT  CAA  CTC  CCT
GAT   ATA  CCT  GCC  GAT  AGC  TTT  TTT  ATC  CCG  CTGGACCAT
GGC   GGA  GTA  AAT  TTT  GAA
ATC   CAG  GTG  GAT  ACG  GAT  GCG  ACC  GAA  ATT  ATACTCCAT
GAG   CTG  AAA  GAA  GGA  AAT
TCT   GAA  TCT  CGT  TCG  GTG  CAA  TTA  AAT  ACG  CCAATACAG
GTC   GGT  GAA  TTG  CTT  ATC
CTG   ATT  CGC  CCG  GAA  AGC  GAG  CCG  TGG  GTG  CCCGAGCAG
CCT   GAG  AAG  TTA  GAA  ACG
TCT   GCA  AAA  AAG  AAC  GAG  CCG  CGT  TTT  AAA  AACGGAATT
GTA   GCA  GCA  CTG  GCC
GGG   TTT  TTT  ATA  TTG  GGA  ATT  GGG  ACT  GTG  GGGACGTTA
TGG   ATA  CTT  AAC  TCG  CCG
CAG   CGG  CAG  GCC  CGA  GAG  CTC  GAT  TCG  TTA  TTGGGGCAG
GAG   AAG  GAG  CGT  TTT  CAG  GTG       TTG  CCA  GGCC 3'
```

FIG. 5

SALMONELLA VIRULENCE GENES

This application is a divisional of application Ser. No. 08/090,526, filed Jul. 9, 1993, now U.S. Pat. No. 5,599,537, which is a continuation-in-part of application Ser. No. 07/629,602, filed Dec. 18, 1990, now abandoned.

This invention was made in the course of work supported by the United States Government, which has certain rights in the invention.

BACKGROUND OF THE INVENTION

Enteric fevers and diarrheal diseases, e.g., typhoid fever and cholera, are major causes of morbidity and mortality throughout the developing world, Hook et al., 1980, In Harrison's Principles of Internal Medicine, 9th Ed., 641–848, McGraw Hill, New York. Traditional approaches to the development of vaccines for bacterial diseases include the parenteral injection of purified components or killed organisms. These parenterally administered vaccines require technologically advanced preparation, are relatively expensive, and are often, because of dislike for needle-based injections, resisted by patients. Live oral vaccine strains have several advantages over parenteral vaccines: low cost, ease of administration, and simple preparation.

The development of live vaccines has often been limited by a lack of understanding of the pathogenesis of the disease of interest on a molecular level. Candidate live vaccine strains require nonrevertable genetic alterations that affect the virulence of the organism, but not its induction of an immune response. Work defining the mechanisms of toxigenesis of *Vibrio cholerae* has made it possible to create live vaccine strains based on deletion of the toxin genes, Mekalanos et al., 1983, Nature 306:551, Levine et al., 1988, Infect. Immun. 56:161.

Recent studies have begun to define the molecular basis of *Salmonella typhimurium* macrophage survival and virulence, Miller et al., 1989, Proc. Natl. Acad. Sci. U.S.A. 86:5054, hereby incorporated by reference. *Salmonella typhimurium* strains with mutations in the positive regulatory regulon phoP are markedly attenuated in virulence for BALB/c mice. The phoP regulon is composed of two genes present in an operon, termed phoP and phoQ. The phoP and phoQ gene products are highly similar to other members of bacterial two-component transcriptional regulators that respond to environmental stimuli and control the expression of a large number of other genes. A mutation at one of these phoP regulatory region regulated genes, pagC, confers a virulence defect. Strains with pagC, phoP, or phoQ mutations afford partial protection to subsequent challenge by wild-type *S. typhimurium*.

Salmonella species cause a spectrum of clinical disease that includes enteric fevers and acute gastroenteritis, Hook et al., 1980, supra. Infections with Salmonella species are more common in immunosuppressed persons, Celum et al., 1987, J. Infect. Dis. 156:998. *S. typhi*, the bacterium that causes typhoid fever, can only infect man, Hook et al., 1980, supra. The narrow host specificity of *S. typhi* has resulted in the extensive use of *S. enteriditis typhimurium* infection of mice as a laboratory model of typhoid fever, Carter et al., 1984 J. Exp. Med. 139:1189. *S. typhimurium* infects a wider range of hosts, causing acute gastroenteritis in man and a disease similar to typhoid fever in the mouse and cow.

Salmonella infections are acquired by oral ingestion. The organisms, after traversing the stomach, replicate in the small bowel, Hornik et al., 1970, N. Eng. J. Med. 283:686. Salmonella are capable of invasion of the intestinal mucosal cells, and *S. typhi* can pass through this mucosal barrier and spread via the Peyer's patches to the lamina propria and regional lymph nodes. Colonization of the reticuloendothelial cells of the host then occurs after bacteremia. The ability of *S. typhi* to survive and replicate within the cells of the human reticuloendothelial system is essential to its pathogenesis, Hook et al., 1980, supra, Hornick et al., 1970, supra, and Carter et al., 1984, supra.

Immunity to *Salmonella typhi* involves humoral and cell-mediated immunity, Murphy et al., 1987, J. Infect. Dis. 156:1005, and is obtainable by vaccination, Edelman et al., 1986, Rev. Inf. Dis. 8:324. Recently, human field trials demonstrated significant protective efficacy against *S. typhi* infection after intramuscular vaccination with partially purified Vi antigen, Lanata et al., 1983, Lancet 2:441. Antibody-dependent enhancement of *S. typhi* killing by T cells has been demonstrated in individuals who received a live *S. typhi* vaccine, indicating that these antibodies may be necessary for the host to generate a cell-mediated immune response, Levine et al., 1987, J. Clin. Invest. 79:888. The cell-mediated immune response is important in typhoid immunity since killed vaccines that do not induce this immune response are not protective in man, Collins et al., 1972, Infect. Immun. 41:742.

SUMMARY OF THE INVENTION

In general, the invention features a vaccine, preferably a live vaccine, including a bacterial cell, preferably a Salmonella cell, e.g., a *S. typhi, S. enteritidis typhimurium*, or *S. cholerae-suis* cell, the virulence of which is attenuated by the constitutive expression of a gene under the control of a two-component regulatory system. In preferred embodiments the constitutive expression is the result of a mutation at a component of the two-component regulatory system. In preferred embodiments the bacterial cell includes a second mutation which attenuates virulence.

In yet other preferred embodiments of the vaccine the two-component regulatory system is the phoP regulatory region, and the gene under the control of the two-component system is a phoP regulatory region regulated gene, e.g., a prg gene, e.g., prgA, prgB, prgC, prgE, or prgH, or pag gene, e.g., pagC. In preferred embodiments constitutive expression is the result of a change or mutation (preferably a non-revertible mutation) at the promoter of the regulated gene or of the phoP regulatory region, e.g., a mutation in the phoQ or the phoP gene, e.g., the phoP$^c$ mutation.

In another aspect, the invention features a vaccine including a bacterial cell which is attenuated by decrease of expression of a virulence gene under control of a phoP regulatory region, e.g., a prg gene, e.g., prgA, prgB, prgC, prgE, or prgH.

In preferred embodiments of the vaccine the Salmonella cell includes a first mutation which attenuates virulence, e.g., a mutation in a phoP regulatory region gene, e.g., a mutation in the phoP or phoQ gene, e.g., phoP$^c$, or a mutation in a phoP regulatory region regulated gene, and a second mutation which attenuates virulence, e.g., a mutation in an aromatic amino acid synthetic gene, e.g., an aro gene, a mutation in a phoP regulatory region regulated gene, e.g., a mutation in a prg gene, e.g., prgA, prgB, prgC, prgE, or prgH, or pag locus, e.g., a pagC mutation.

In yet other preferred embodiments the bacterial cell includes a first mutation in a phoP regulatory region gene and a second mutation in an aromatic amino acid synthetic gene, e.g, an aro gene.

In another aspect, the invention features a vaccine, preferably a live vaccine, including a bacterial cell, the virulence of which is attenuated by a mutation in a gene under the control of a two-component regulatory system. In preferred embodiments the bacterial cell includes a virulence attenuating mutation in a second gene, e.g., in an aromatic amino acid-synthetic gene, e.g., an aro gene.

In yet other preferred embodiments of the vaccine the bacterial cell is Salmonella cell, the two-component regulatory system is the phoP regulatory region, and the gene under its control is a prg gene, e.g. prgA, prgB, prgC, prg-E, or prgH, or a pag gene, e.g., the pagC gene.

In another aspect the invention features a vaccine, preferably a live vaccine, including a Salmonella cell e.g., a *S. typhi, S. enteritidis typhimurium*, or *S. cholerae-suis* cell, including a first virulence attenuating mutation in an aromatic amino acid biosynthetic gene, e.g., an aro gene, and a second virulence attenuating mutation in a phoP regulatory region gene, e.g., a phoP$^-$ mutation.

In another aspect the invention features a bacterial cell, or a substantially purified preparation thereof, preferably a Salmonella cell, e.g., a *S. typhi, S. enteritidis typhimurium*, or *S. cholerae-suis* cell, which constitutively expresses a gene under the control of a two-component regulatory system and which includes a virulence attenuating mutation which does not result in constitutive expression of a gene under the control of the two-component regulatory system. In preferred embodiments the bacterial cell includes a mutation in a component of the two-component regulatory system.

In preferred embodiments the bacterial cell is a Salmonella cell which expresses a phoP regulatory region regulated gene constitutively (the constitutive expression preferably caused by a mutation, preferably a non-revertible mutation, e.g., a deletion in the phoP regulatory region, e.g., a mutation in the phoQ or phoP gene, e.g., phoP$^c$), and which includes a virulence attenuating mutation, preferably a non-revertible mutation, e.g., a deletion, preferably in an aromatic amino acid synthetic gene, e.g., an aro gene, or in a phoP regulatory region regulated gene, e.g., a prg gene, e.g., prgA, prgB, prgC, prgE, or prgH or pag gene, e.g., pagC which does not result in the constitutive expression of a gene under the control of the phoP regulatory region.

In another aspect, the invention features a bacterial cell, or a substantially purified preparation thereof, e.g., a Salmonella cell, e.g., a *S. typhi* cell, an *S. enteritidis typhimurium* or a *S. cholerae-suis* cell, including a virulence attenuating mutation in a gene regulated by a two-component regulatory system. In preferred embodiments the virulence attenuating mutation is in a phoP regulatory region regulated gene, e.g., a prg gene, e.g., prgA, prgB, prgC, prgE, or prgH or pag gene, e.g., pagC.

In preferred embodiments the bacterial cell includes a second mutation, e.g., in an aromatic amino acid synthetic gene, e.g., an aro gene, in a phoP regulatory region gene, e.g., the phoP or phoQ genes, or in a phoP regulating region regulated gene, e.g., a prg gene, e.g., prgA, prgB, prgC, prgE, or prgH or a pag gene, e.g., pagC, which attenuates virulence but which does not result in constitutive expression of a phoP regulatory region regulated gene.

The invention also features a live Salmonella cell, or a substantially purified preparation thereof, e.g., a *S. typhi, S. enteritidis typhimurium*, or *S. cholerae-suis* cell, in which there is inserted into a virulence gene, e.g., a gene in the phoP regulating region, or a phoP regulating region regulated gene, e.g., a prg gene, e.g., prgA, prgB, prgC, prgE, or prgH or a pag locus, e.g., pagC, a gene encoding a heterologous protein, or a regulatory element thereof.

In preferred embodiments the live Salmonella cell carries a second mutation, e.g., an aro mutation, e.g., an aroA mutation, e.g., aroA$^-$ or aroADEL407, that attenuates virulence.

In preferred embodiments the DNA encoding a heterologous protein is under the control of an environmentally regulated promoter. In other preferred embodiments the live Salmonella cell further includes a DNA sequence encoding T7 polymerase under the control of an environmentally regulated promoter and a T7 transcriptionally sensitive promoter, the T7 transcriptionally sensitive promoter controlling the expression of the heterologous antigen.

The invention also features a vector capable of integrating into the chromosome of Salmonella including: a first DNA sequence encoding a heterologous protein; a second (optional) DNA sequence encoding a marker e.g., a selective marker, e.g., a gene that confers resistance for a heavy metal resistance or a gene that complements an auxotrophic mutation carried by the strain to be transformed; and a third DNA sequence, e.g., a phoP regulon encoded gene, e.g., a prg gene, e.g., prgA, prgB, prgC, prgE, or prgH or a pag locus, e.g., pagC, encoding a phoP regulatory region regulated gene product necessary for virulence, the third DNA sequence being mutationally inactivated.

In other preferred embodiments: the first DNA sequence is disposed on the vector so as to mutationally inactivate the third DNA sequence; the vector cannot replicate in a wild-type Salmonella strain; the heterologous protein is under the control of an environmentally regulated promoter; and the vector further includes a DNA sequence encoding T7 polymerase under the control of an environmentally regulated promoter and a T7 transcriptionally sensitive promoter, the T7 transcriptionally sensitive promoter controlling the expression of the heterologous antigen.

In another aspect the invention includes a method of vaccinating an animal, e.g., a mammal, e.g., a human, against a disease caused by a bacterium, e.g., Salmonella, including administering a vaccine of the invention.

The invention also includes a vector including DNA which encodes the pagC gene product; a cell transformed with the vector; a method of producing the pagC gene product including culturing the transformed cell and purifying the pagC gene product from the cell or culture medium; and a purified preparation of the pagC gene product.

In another aspect the invention includes a method of detecting the presence of Salmonella in a sample including contacting the sample with pagC encoding DNA and detecting the hybridization of the pagC encoding DNA to nucleic acid in the sample.

The invention also includes a vector including DNA which encodes the prgH gene product; a cell transformed with the vector; a method of producing the prgH gene product including culturing the transformed cell and purifying the prgH gene product from the cell or culture medium; and a purified preparation of the prgH gene product.

In another aspect the invention includes a method of detecting the presence of Salmonella in a sample including contacting the sample with prgH encoding DNA and detecting the hybridization of the prgH encoding DNA to nucleic acid in the sample.

In another aspect the invention features a method of attenuating the virulence of a bacterium, the bacterium including a two-component regulatory system, including causing a gene under the control of the two-component system to be expressed constitutively. In preferred embodiments the bacterium is Salmonella, e.g., *S. typhi, S. enteritidis typhimurium,* or *S. cholerae-suis,* and the two-component system is the phoP regulatory region.

Two-component regulatory system, as used herein, refers to a bacterial regulatory system that controls the expression of multiple proteins in response to environmental signals. The two-components referred to in the term are a sensor, which may, e.g., sense an environmental parameter and in response thereto promote the activation, e.g. by promoting the phosphorylation, of the second component, the activator. The activator affects the expression of genes under the control of the two-component system. A two-component system can include, e.g., a histidine protein kinase and a phosphorylated response regulator, as is seen in both gram positive and gram negative bacteria. In *E. coli,* e.g., 10 kinases and 11 response regulators have been identified. They control chemotaxis, nitrogen regulation, phosphate regulation, osmoregulation, sporulation, and many other cellular functions, Stock et al., 1989 Microbiol. Rev. 53:450–490, hereby incorporated by reference. A two-component system also controls the virulence of *Agrobacterium tumefasciens* plant tumor formation, Leroux et al. EMBO J 6:849–856, hereby incorporated by reference). Similar virulence regulators are involved in the virulence of *Bordetella pertussis* Arico et al., 1989, Proc. Natl. Acad. Sci. U.S.A. 86:6671–6675, hereby incorporated by reference, and *Shigella flexneri,* Bernardini et al., 1990, J. Bact. 172:6274–6281, hereby incorporated by reference.

Environmentally regulated, as used herein refers to a pattern of expression wherein the expression of a gene in a cell depends on the levels of some characteristic or component of the environment in which the cell resides. Examples include promoters in biosynthetic pathways which are turned on or off by the level of a specific component or components, e.g., iron, temperature responsive promoters, or promoters which are expressed more actively in specific cellular compartments, e.g., in macrophages or vacuoles.

A vaccine, as used herein, is a preparation including materials that evoke a desired biological response, e.g., an immune response, in combination with a suitable carrier. The vaccine may include live organism, in which case it is usually administered orally, or killed organisms or components thereof, in which case it is usually administered parenterally. The cells used for the vaccine of the invention are preferably alive and thus capable of colonizing the intestines of the inoculated animal.

A mutation, as used herein, is any change (in comparison with the appropriate parental strain) in the DNA sequence of an organism. These changes can arise e.g., spontaneously, by chemical, energy e.g., X-ray, or other forms of mutagenesis, by genetic engineering, or as a result of mating or other forms of exchange of genetic information. Mutations include e.g., base changes, deletions, insertions, inversions, translocations or duplications.

A mutation attenuates virulence if, as a result of the mutation, the level of virulence of the mutant cell is decreased in comparison with the level in a cell of the parental strain, as measured by (a) a significant (e.g., at least 50%) decrease in virulence in the mutant strain compared to the parental strain, or (b) a significant (e.g., at least 50%) decrease in the amount of the polypeptide identified as the virulence factor in the mutant strain compared to the parental strain.

A non-revertible mutation, as used herein, is a mutation which cannot revert by a single base pair change, e.g., deletion or insertion mutations and mutations that include more than one lesion, e.g., a mutation composed of two separate point mutations.

The phoP regulatory region, as used herein, is a two-component regulatory system that controls the expression of pag and prg genes. It includes the phoP locus and the phoQ locus.

phoP regulatory region regulated genes, as used herein, refer to genes such as pag and prg genes.

pag, as used herein, refers to a gene which is positively regulated by the phoP regulon.

prg, as used herein, refers to a gene which is negatively regulated by the phoP regulon.

An aromatic amino acid synthetic gene, as used herein, is a gene which encodes an enzyme which catalyzes a step in the synthesis of an aromatic amino acid. aroA, aroC, and aroD are examples of such genes in Salmonella. Mutations in these genes can attenuate virulence without the total loss of immunogenicity.

Abnormal expressions, as used herein, means expression which is higher or lower than that seen in wild type.

Heterologous protein, as used herein, is a protein that in wild type, is not expressed or is expressed from a different chromosomal site, e.g., a heterologous protein is one encoded by a gene that has been inserted into a second gene.

Virulence gene, as used herein, is a gene the inactivation of which results in a Salmonella cell with less virulence than that of a similar Salmonella cell in which the gene is not inactivated. Examples include the phoP, pagC, prgH genes.

A marker, as used herein, is gene product the presence of which is easily determined, e.g., a gene product that confers resistance to a heavy metal or a gene product which allows or inhibits growth under a given set of conditions.

Purified preparation, as used herein, is a preparation, e.g., of a protein, which is purified from the proteins, lipids, and other material with which it is associated. The preparation is preferably at least 2–10 fold purified.

Constitutive expression, as used herein, refers to gene expression which is modulated or regulated to a lesser extent than the expression of the same gene in an appropriate control strain, e.g., a parental or in wild-type strain. For example, if a gene is normally repressed under a first set of conditions and derepressed under a second set of conditions constitutive expression would be expression at the same level, e.g., the repressed level, the derepressed level, or an intermediate level, regardless of conditions. Partial constitutive expression is included within the definition of constitutive expression and occurs when the difference between two levels of expression is reduced in comparison in what is seen in an appropriate control strain, e.g., a wild-type or parental strain.

A substantially purified preparation of a bacterial cell is a preparation of cells wherein contaminating cells without the desired mutant genotype constitute less than 10%, preferably less than 1%, and more preferably less than 0.1% of the total number of cells in the preparation.

The invention allows for the attenuation of virulence of bacteria and of vaccines that include bacteria, especially vaccines that include live bacteria, by mutations in two-component regulatory systems and/or in genes regulated by these systems. The vaccines of the invention are highly attenuated for virulence but retain immunogenicity, thus they are both safe and effective.

The vectors of the invention allow the rapid construction of strains containing DNA encoding heterologous proteins, e.g., antigens. The heterologous protein encoding DNA is chromosomally integrated, and thus stable, unlike plasmid systems which are dependent on antibiotic resistance or other selection pressure for stability. Live Salmonella cells of the invention in which the expression of heterologous protein is under the control of an environmentally responsive promoter do not express the heterologous protein at times when such expression would be undesirable e.g., during culture, vaccine preparation, or storage, contributing to the viability of the cells, but when administered to humans or animals, express large amounts of the protein. This is desirable because high expression of many heterologous proteins in Salmonella can be associated with toxicity to the bacterium. The use of only a single integrated copy of the DNA encoding the heterologous protein also contributes to minimal expression of the heterologous protein at times when expression is not desired. In embodiments where a virulence gene, e.g., the pagC gene or the prgH gene, contains the site of integration for the DNA encoding the heterologous protein the virulence of the organism is attenuated.

Other features and advantages of the invention will be apparent from the following description of the preferred embodiments and from the claims.

DESCRIPTION OF THE PREFERRED EMBODIMENTS

The drawings will first be described.

Drawings

FIG. 3 is a map of the DNA sequence of the pagC region (SEQ ID NO:1) and the amino acid sequence of pagC (SEQ ID NO:5).

Figure 4:
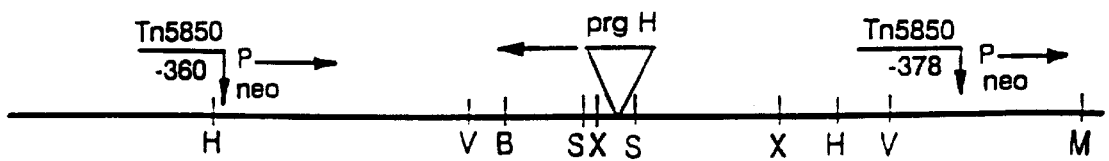

FIG. 4 is a map of the location of prgH within the hil locus. The arrows indicate the direction of orientation of the neomycin promoter of Tn5B5 insertions within the hil locus and the direction of transcription of the prgH1::TnphoA fusion protein. Restriction endonuclease sites are represented by B. BamH1; H, HindIII; X, XhoI; S, SacI; V, EcoRV.

FIG. 5 is a DNA sequence from the prgH gene (plasmid pIB01). (SEQ ID NO:3)

STRAIN DEPOSIT

Under the terms of the Budapest Treaty on the International Recognition of the Deposit of Microorganisms for the Purpose of Patent Procedure, deposit of the following materials has been made with the American Type Culture Collection (ATCC) of Rockville, Md., U.S.A.

Applicant's assignee, Massachusetts General Hospital, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

PhoP$^c$ strain CS022 (described below) has been deposited with the American Type Culture Collection (Rockville, Md.) and has received ATCC designation 55130.

The plasmid, pIB01, containing the prgH gene has been deposited on Jul. 9, 1993 with the American Type Culture Collection (Rockville, Md.) and has received ATCC designation 75496. Constitutive Expression of the PhoP Regulon Attenuates Salmonella Virulence and Survival within Macrophages The phoP constitutive allele (PhoP$^c$), pho-24, results in derepression of pag loci. Using diethyl sulfate mutagenesis of *S. typhimurium* LT-2, Ames and co-workers isolated strain TA2367 pho-24 (all strains, materials, and methods referred to in this section are described below), which contained a phoP locus mutation that resulted in constitutive production of acid phosphatase in rich media, Kier et al., 1979, J. Bacteriol. 138:155, hereby incorporated by reference. This phoP-regulated acid phosphatase is encoded by the phoN gene, a pag locus, Kier et al., 1979, supra, Miller et al., 1989, supra. To analyze whether the pho-24 allele increased the expression of other pag loci the effect of the pho-24 allele on the expression of other pag loci recently identified as transcriptional (e.g., pagA and pagB) and translational (e.g., pagC) fusion proteins that required phoP and phoQ for expression, Miller et al., 1989, supra, was determined. pag gene fusion strains, isogenic except for the pho-24 allele, were constructed and assayed for fusion protein activity. PhoP$^c$ derivatives of the pagA::Mu dJ and pagB::Mu dJ strains produced 480 and 980 U, respectively, of β-galactosidase in rich medium, an increase of 9- to 10-fold over values for the fusion strains with a wild-type phoP locus, see Table 1.

TABLE 1

Bacterial strains and properties

| Strain | Genotype | Enzyme acitivity (U)$^a$ | Reference or source |
|---|---|---|---|
| 10428 | Wild type | 180 (A) | ATCC; Miller et al., 1989, supra |
| TA2367 | pho-24 | 1,925 (A) | Kier et al., 1974, supra |
| CS003 | ΔphoP ΔpurB | <10 (A) | Miller et al., 1989, supra |
| CS022 | pho-24 | 1,750 (A) | This work |
| CS023 | pho-24 phoN2 zxx::6251Tn10d-Cam | 25 (A) | This work |
| CS012 | pagA1::MU dJ | 45 (B) | Miller et al., 1989, supra |
| CS013 | pagB1::MU dJ | 120 (B) | Miller et al., 1989, supra |
| CS119 | pagC1::TnphoA phoN2 zxx::6251Tn10d-Cam | 85 (C) | Miller et al., 1989, supra |
| SC024 | pagA1::MU dJ pho-24 | 450 (B) | This work |
| SC025 | pagB1::MU dJ pho-24 | 980 (B) | This work |
| SC026 | pagC1::TnphoApho-24phoN2 zxx::6251Tn10d-Cam | 385 (B) | This work |

TABLE 1-continued

Bacterial strains and properties

| Strain | Genotype | Enzyme acitivity (U)[a] | Reference or source |
|---|---|---|---|
| CS015 | phoP102::Tn10d-Cam | <10 (A) | Miller et al., 1989, supra |
| TT13208 | phoP105::Tn10d | <10 (A) | —[b] |

[a]A. Acid phosphatase; B, β-galactosidase; C, alkaline phosphatase.
[b]Gift of Ning Zhu and John Roth.

The pagC::TnphoA gene fusion produced 350 U of alkaline phosphatase, an increase of three- to fourfold over that produced in strain CS119, which is isogenic except for the pho-24 mutation, Miller et al., 1989, supra. These results compare with a ninefold increase in the acid phosphatase activity in strain CS022 on introduction of the pho-24 allele. Therefore, these available assays for pag gene expression document that the pho-24 mutation causes constitutive expression of pag loci other than phoN.

Identifications of protein species that are repressed as well as activated in the PhoP[c] mutant strain Whole-cell proteins of strain CS022 were analyzed to estimate the number of protein species that could be potentially regulated by the PhoP regulon. Remarkably, analysis by one-dimensional polyacrylamide gel electrophoresis of the proteins produced by strains with the PhoP[c] phenotype indicated that some protein species were decreased in expression when many presumptive pag gene products were fully induced by the pho-24 mutation. The proteins decreased in the PhoP[c] strain might represent products of genes that are repressed by the PhoP regulator. Genes encoding proteins decreased by the pho-24 allele are designated prg loci, for phoP-repressed genes. Comparison of wild-type, PhoP⁻, and PhoP[c] mutant strain proteins shows that growth in LB medium at 37° C. represents repressing conditions for pag gene products and derepressing conditions for prg gene products.

To estimate the total number of potentially PhoP-regulated gene products, the total cell proteins of wild-type and PhoP[c] mutant strains grown in LB were analyzed by two-dimensional gel electrophoresis. At least 40 species underwent major fluctuation in expression in response to the pho-24 mutation.

Virulence defects of the PhoP[c] strain. Remarkably, strains with the single pho-24 mutation were markedly attenuated for virulence in mice (Table 2). The number of PhoP[c] organisms ($2 \times 10^5$) that killed 50% of BALB/c mice challenged ($LD_{50}$) by the intraperitoneal (i.p.) route was near that ($6 \times 10^5$) of PhoP⁻ bacteria, Miller et al., 1989, supra. The PhoP[c] strains had growth comparable to wild-type organisms in rich and minimal media. The PhoP[c] mutants were also tested for alterations in lipopolysaccharide, which could explain the virulence defect observed. Strain CS022 had normal sensitivity to phage P22, normal group B reactivity to antibody to O antigen, and a lipopolysaccharide profile identical to that of the parent strain, as determined by polyacrylamide gel electrophoresis and staining.

TABLE 2

Virulence and protective efficacy of PhoP[c] and PhoP⁻ Salmonella strains

| Immunizing dose | No. of initial survivors/ total | No. of survivors/total after wild-type challenge dose of: | | | |
|---|---|---|---|---|---|
| | | $5 \times 10^7$ | $5 \times 10^5$ | $5 \times 10^4$ | $5 \times 10^3$ |
| PhoP[c] organisms | | | | | |
| 15 | 13/13 | | 5/5 | 4/5 | |
| 50 | 4/4 | | | | 4/4 |
| $1.5 \times 10^2$ | 11/11 | | 4/4 | 3/3 | |
| $5 \times 10^2$ | 16/16 | | | | 4/4 |
| $1.5 \times 10^3$ | 5/5 | | 3/3 | 2/2 | |
| $5 \times 10^3$ | 4/4 | | | | 4/4 |
| $1.5 \times 10^4$ | 5/5 | | 3/3 | 2/2 | |
| $5 \times 10^4$ | 19/23 | | | | 4/4 |
| $1.5 \times 10^5$ | 5/5 | | 3/3 | 2/2 | |
| $5 \times 10^5$ | 1/4 | | | | 1/1 |
| $5 \times 10^6$ | 0/6 | | | | |
| $3 \times 10^9$ (*) | 5/5 | 5/5 | | | |
| $3 \times 10^{10}$ (*) | 5/5 | 5/5 | | | |
| $1.5 \times 10^{11}$ (*) | 5/5 | 5/5 | | | |
| PhoP⁻ organisms | | | | | |
| $6 \times 10^3$ | 36/36 | | 0/12 | 0/12 | 0/12 |
| $6 \times 10^4$ | 36/36 | | 0/12 | 0/12 | 3/12 |
| $6 \times 10^5$ | 19/36 | | 0/6 | 0/6 | 4/7 |
| $5 \times 10^{10}$ (*) | 7/7 | 3/7 | | | |

(*) Organisms were administered by the oral route. In all other experiments, organisms were administered by i.p. challenge.

Since the TA2367 pho-24 strain was constructed by chemical mutagenesis and could have another linked mutation responsible for its virulence defect revertants of the PhoP[c] were isolated to determine whether the pho-24 allele was responsible for the attenuation of virulence observed. Phenotype PhoP[c] revertants, identified by the normal levels of acid phosphatase in rich medium, were isolated among the bacteria recovered from the livers of mice infected with strain CS022. Six separate phenotypic revertants, designated CS122 to CS128, were found to be fully virulent ($LD_{50}$ of less than 20 organisms for BALB/c mice). The locus responsible for the reversion phenotype was mapped in all six revertants tested for virulence by bacteriophage P22 cotransduction and had linkage characteristics consistent with the phoP locus (greater than 90% linkage to purB). These data indicate that these reversion mutations are not extragenic suppressors but are intragenic suppressors or true revertants of the pho-24 mutation. Thus, the virulence defect of PhoP[c] mutants is probably the result of a single revertible mutation in the phoP locus and not the result of a second unrelated mutation acquired during mutagenesis.

Reversion frequency of the PhoP[c] phenotype. The reversion frequency of the PhoP[c] mutation in vivo in mice was investigated to assess whether reversion could reduce the $LD_{50}$ of this strain. The presence of the revertants of strain CS022 was tested for by administering $10^6$, $10^4$, and $10^2$ challenge organisms to each of eight animals by i.p. injection. On day 7, three animals died that received $10^6$ PhoP[c] organisms. On that day, the livers and spleens of all animals were harvested and homogenized in saline. After appropriate dilution, 10% of the tissue was plated on LB plates containing the chromogenic phosphatase substrate XP. Revertants were identified by their lighter blue colonies compared with PhoP[c] bacteria and were confirmed by quantitative acid phosphatase assays. An estimated $10^7$, $10^5$, and $10^3$ organisms per organ were recovered from animals at each of the three respective challenge doses. Revertants were identified only at the highest dose and comprised 0.5 to 1%, or $10^5$ organisms per organ, at the time of death. It is likely that revertants are able to compete more effectively for growth in these macrophage-containing organs, since strain CS022 is deficient in survival within macrophages (see below). However, revertants were not identified if fewer than $10^5$ organisms were administered in the challenge dose, suggesting that the reversion frequency must be approximately $10^{-5}$. The reversion rate of the $PhoP^c$ phenotype for CS022 bacteria grown in LB is in fact $6 \times 10^{-4}$ when scored by the same colony phenotypes. The percentage of revertants recovered from animals near death suggests that pressure is applied in vivo that selects for revertants of the $PhoP^c$ phenotype and implies that the virulence defect observed could be much greater quantitatively for a strain with a nonrevertible $PhoP^c$ mutation.

Figure 1:
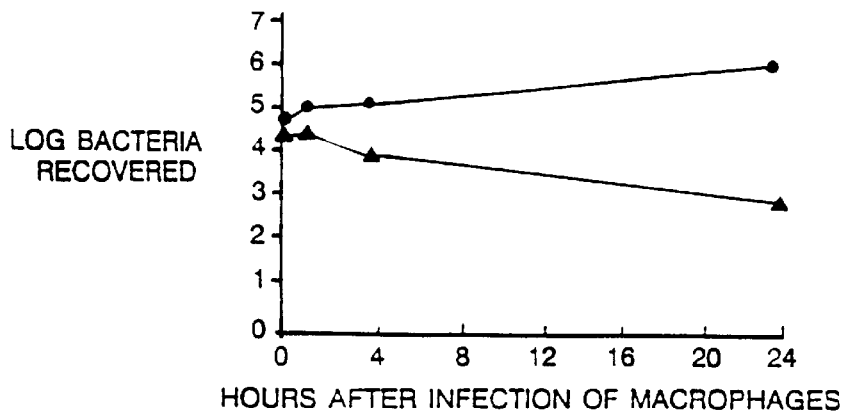
FIG. 1 is a graph of the survival of Salmonella strains within macrophages.

The $PhoP^c$ strain is deficient in survival within macrophages. Because of the importance of survival within macrophages to Salmonella virulence Fields et al., 1986, Proc. Natl. Acad. Sci. U.S.A. 83:5189, hereby incorporated by reference, $PhoP^c$ bacteria were tested for this property. Strain CS022 was defective in the ability to grow and persist in macrophages as compared with wild-type organisms (FIG. 1). In FIG. 1 the survival of strain CS022 ($PhoP^c$) (triangles) in cultured macrophages is compared with that of wild-type S. typhimurium ATCC 10428 (cicles). The experiment shown is a representative one. The difference between the two strains at 4 and 24 hours is significant ($P < 0.05$). $PhoP^-$ bacteria seemed to have a macrophage survival defect qualitatively similar to that of $PhoP^c$ bacteria but survived consistently better by two- to threefold in side-by-side experiments. The increased recovery of organisms that reverted to $PhoP^c$ phenotype in mouse organs rich in macrophage content is consistent with the reduced macrophage survival of $PhoP^c$ mutants in vitro.

Use of the $PhoP^c$ strain as a live vaccine. It has been previously reported that $PhoP^-$ strains are useful as live vaccines in protecting against mouse typhoid, Miller et al., 1989, supra. The immunogenicity of $PhoP^c$ when used as live attenuated vaccines in mice was compared with that of $PhoP^-$. This was done by simultaneous determination of survival, after graded challenge doses with the wild-type strain ATCC 10428, in mice previously immunized with graded doses of the two live vaccine strains. CS015 phoP::Tn10d-Cam and CS022 pho-24, as well as a saline control. The results obtained (Table 2) suggest the following conclusions: (i) small i.p. doses of the $PhoP^c$ strain (e.g., 15 organisms) effectively protect mice from challenge doses as large as $5 \times 10^5$ bacteria (a challenge dose that represents greater than $10^4$ i.p. $LD_{50}$s), (ii) large doses of $PhoP^c$ organisms given orally completely protect mice from an oral challenge consisting of $5 \times 10^7$ wild-type bacteria (over 200 oral wild-type $LD_{50}$s) and (iii) by comparison, a large dose of $PhoP^-$ organisms ($5 \times 10^5$) does not provide similar protection. The reversion of the $PhoP^c$ mutation in vivo somewhat complicates the analysis of the use of these strains as vaccines, since revertants of the CS022 strain (i.e., wild-type cells) could increase immunogenicity). However, we were unable to identify revertants by examining 10% of the available spleen and liver tissue from those mice that received $10^4$ or fewer organisms.

Strains Materials and Methods. The strains, materials, and methods used in the PhoP regulon work described above are as follows.

American Type Culture Collection (ATCC) strain 14028, a smooth virulent strain of S. typhimurium, was the parent strain for all virulence studies. Strain TT13208 was a gift from Nang Zhu and John Roth. Strain TA2367 was a generous gift of Gigi Stortz and Bruce Ames, Kier et al., 1979, supra. Bacteriophage P22HT int was used in transductional crosses to construct strains isogenic except for phoP locus mutations, Davis et al., 1980, Advanced Bacterial Genetics, p. 78, 87. Cold Spring Harbor Laboratory, Cold Spring Harbor, N.Y., hereby incorporated by reference. Luria broth was used as rich medium, and minimal medium was M9, Davis et al., 1980, supra. The chromogenic phosphatase substrate 5-bromo-4-chloro-3indolyl phosphate (XP) was used to qualitatively access acid and alkaline phosphatase production in solid media.

Derivatives of S. typhimurium ATCC 10428 with the pho-24 mutation were constructed by use of strain TA2367 as a donor of the purB gene in a P22 transductional cross with strain CS003 ΔphoP ΔpurB, Miller et al., 1989, supra. Colonies were then selected for the ability to grow on minimal medium. A transductant designated CS022 (phenotype $PhoP^c$) that synthesized 1,750 U of acid phosphatase in rich medium (a ninefold increase over the wild-type level in rich medium) was used in further studies.

Derivatives of strains CS022 and CS023 pho-24 phoN2 zxx::6251Tn10d-Cam, and acid phosphatase-negative derivative of CS022, containing pag gene fusions were constructed by bacteriophage P22 transductional crosses, using selection of TnphoA- or Mu dJ-encoded kanamycin resistance. Strains were checked for the intact pag gene fusion by demonstration of appropriate loss of fusion protein activity on introduction of a phoP105::Tn10d or phoP102::Tn10d-Cam allele.

Assays of acid phosphatase, alkaline phosphatase, and β-galactosidase were performed as previously described, Miller et al., 1989, supra and are reported in units as defined in Miller, 1972, Experiments in molecular genetics, p. 352–355, Cold Spring Harbor Laboratory, Cold Spring Harbor, N.Y., hereby incorporated by reference.

In the mouse virulence and vaccination studies bacteria grown overnight in Luria broth were washed and diluted in normal saline. The wild-type parent strain of CS022 (ATCC 10428) was used for all live vaccine challenge studies. This strain has a 50% lethal dose ($LD_{50}$) for naive adult BALB/c mice of less than 20 organisms when administered by intraperitoneal (i.p.) injection and $5 \times 10^4$ when administered orally in NaHCO$_3$. Mice were purchased from Charles River Breeding Laboratories, Inc. (Wilmington, Mass.) and were 5 to 6 weeks of age at initial challenge. All i.p. inoculations were performed as previously described, Miller et al., 1989, supra. Oral challenge experiments were performed with bacteria grown in LB broth and concentrated by centrifugation. The bacteria were resuspended in 0.1M NaHCO$_3$ to neutralize stomach acid, and administered as a 0.5-ml bolus to animals under ether anesthesia. Colony counts were performed to accurately access the number of organisms administered. All challenge experiments were performed 1 month after i.p. inoculation and 6 weeks after oral challenge. Challenge inocula were administered by the same route as vaccinations. The care of all animals was under institutional guidelines as set by the animal are committees at the Massachusetts General Hospital and Harvard Medical School.

Protein electrophoresis was performed as follows. One-dimensional protein gel electrophoresis was performed by the method of Laemmli, 1970, Nature 227:680, hereby incorporated by reference, on whole-cell protein extracts of stationary-phase cells grown overnight in Luria broth. The gels were fixed and stained with Coomassie brilliant blue R250 in 10% acetic acid-10% methanol. Two-dimensional protein gel electrophoresis was performed by method of O'Farrell, 1975, J. Biol. Chem. 250:4007, hereby incorporated by reference, on the same whole-cell extracts. Isoelectric focusing using 1.5% pH 3.5 to 10 ampholines (LKB Instruments, Baltimore, Md.) was carried out for 9,600 V h (700 V for 13 h 45 min). The final tube gel pH gradient extended from pH 4.1 to pH 8.1 as measured by a surface pH electrode (BioRad Laboratories, Richmond, Calif.) and colored acetylated cytochrome pI markers (Calbiochem-Behring, La Jolla, Calif.) run in an adjacent tube. The slab gels were silver stained, Merril et al., 1984, Methods Enzymol. 104:441, hereby incorporated by reference.

In the macrophage survival assays experiments were performed as previously described, Miller et al., 1989, supra, by the method of Buchmeier et al., 1989, Infect. Immun. 57:1, hereby incorporated by reference, as modified from the method of Lissner et al, 1983, J. Immunol. 131:3006, hereby incorporated by reference. Stationary-phase cells were opsonized for 30 min in normal mouse serum before exposure to the cultured bone marrow-derived macrophages harvested from BALB/c mice. One hour after infection, gentamicin sulfate (8 μg/ml) was added to kill extracellular bacteria. All time points were done in triplicate and repeated on three separate occasions.

PhoP$^c$ Mutant Strains Are More Effective as Live Vaccines

PhoP$^c$ mutant S. typhimurium are very effective when used as a live vaccine against mouse typhoid fever and are superior to PhoP$^-$ bacteria. As few a 15 PhoP$^c$ bacteria protect mice against $10^5$ LD$_{50}$ (lethal doses 50%) of wild type organisms by the intraperitoneal route (Table 3). This suggests that pag gene products are important antigens for protective immunity against mouse typhoid. Preliminary results have documented that antigens recognized by serum of chronic typhoid carriers recognizes some phoP-regulated gene products of S. typhi. If protective antigens are only expressed within the host, then dead vaccines only grown in rich media may not induce an immune response against these proteins.

The use of different S. typhimurium dead vaccine preparations containing different mutations in the phoP regulon was evaluated. As can be seen in Table 3 no dead cell preparations (even those containing mixtures of PhoP$^-$ and PhoP$^c$ bacteria) are as effective vaccines as are live bacteria. This suggests that there are other properties of live vaccines that increase immunogenicity or that important non-PhoP-regulated antigens are not in these preparations. The only protection observed in any animals studied was at the lowest challenge dose for those immunized with PhoP$^c$ bacteria. This further suggests that phoP activated genes are important protective antigens.

TABLE 3

Salmonella with phoP regulon mutations used as a dead vaccine

| Strain | Vaccination phenotype | Challenge dose of wild type organisms | |
|---|---|---|---|
| | | 6 × 10$^3$ | 6 × 10$^5$ |
| None | | (3) | (5) |
| ATCC10428 | wild type | (8) | (9) |
| CS015 | PhoP$^-$ | (10) | (13) |
| CS022 | PhoP$^c$ | 2/7(*) | (14) |
| CS022/CS015 | PhoP$^-$/PhoP$^c$ | (8) | (13) |

CS015 = phoP102::Tn10d-Cam
CS022 = pho-24

TABLE 3-continued

Salmonella with phoP regulon mutations used as a dead vaccine

| Strain | Vaccination phenotype | Challenge dose of wild type organisms | |
|---|---|---|---|
| | | 6 × 10$^3$ | 6 × 10$^5$ |

BALB/c mice were immunized twice, 7 days apart, with 5 × 10$^8$ formalin-killed bacteria. Three weeks after the second vaccination, mice were challenged with wild-type organisms at the two doses indicated. The numbers in parentheses indicate no survivors after challenge and mean number of days until death
(*) Ratio of survivors to number challenged.
phoP$^c$ indicates the constitutive unregulated expression of phoP-activated genes and lack of expression of phoP repressed genes.
phoP$^-$ indicates a lack of expression of phoP-activated genes and expression of phoP repressed genes.

aroA PhoP Regulon Double Mutant Strains

Recent efforts by Stocker, Levine, and colleagues have focused on the use of strains with auxotrophic mutations in aromatic amino acid and purine pathways as live vaccines, Hoseith et al., 1981, Nature 291:238, hereby incorporated by reference, Stocker, 1988, Vaccine 6:141, hereby incorporated by reference, and Levine et al., 1987, J. Clin. Invest. 79:888, hereby incorporated by reference. Purine mutations were found to be too attenuating for immunogenicity, likely because purines are not available to the organism within the mammalian host, Sigwart et al., 1989, Infect. Immun. 57:1858, hereby incorporated by reference. Because auxotrophic mutations may be complemented by homologous recombination events with wild type copies donated from environmental organisms or by acquiring the needed metabolite within the host, it would seem prudent for live vaccines to contain a second attenuating mutation in a different virulence mechanism, (i.e., not just a second mutation in the same metabolic pathway). Additionally, in mice the aroA mutants have some residual virulence. Various strains with aroA mutations combined with phoP regulon mutations were investigated for virulence attenuation and immunogenicity. Table 4 demonstrates that a PhoP$^-$ or PhoP$^c$ mutation further attenuates aroA mutant S. typhimurium by at least 100-fold and that, at least at high levels of vaccinating organisms, immunogenicity is retained. Strains with both a pagC$^-$ and phoP$^c$ phenotype are also further attenuated than either mutation alone. Therefore, phoP regulon mutations may increase the safety of aroA live vaccine preparations.

TABLE 4A

Additional attenuation of aroA mutants by PhoP regulon mutations

| | | Survivors of varying numbers of Salmonella mutant organisms (*) | | | | |
|---|---|---|---|---|---|---|
| Strain | Phenotype | 10$^6$ | 10$^7$ | 10$^8$ | 10$^9$ | 10$^{10}$(**) |
| CS004 | aroA- | 6/6 | 1/6 | 0/6 | 0/6 | 6/6 |
| SL3261 | aroAdel His$^-$ | 6/6 | 1/6 | 0/6 | 0/6 | 6/6 |
| CS322 | aroA- PhoP$^c$ | 6/6 | 6/6 | 6/6 | 1/6 | 6/6 |
| CS323 | S13261 PhoP$^c$ | 6/6 | 6/6 | 6/6 | 2/6 | 6/6 |
| CS315 | aroA- PhoP$^-$ | 6/6 | 6/6 | 6/6 | 2/6 | 6/6 |
| CS316 | SL3261 PhoP$^-$ | 6/6 | 6/6 | 6/6 | 1/6 | 6/6 |
| CS026 | pagC$^-$ PhoP$^c$ | 6/6 | 4/6 | 0/6 | 0/6 | 6/6 |

TABLE 4B

Protective efficacy of Salmonella with aroA/phoP regulon mutations

| | | | Survivors of challenge doses of wild type organisms (*) | |
|---|---|---|---|---|
| Strain | Phenotype | Inoculum | $5 \times 10^5$ | $5 \times 10^7$ |
| CS004 | aroA⁻ | $10^6$ | 4/4 | 5/5 |
| SL3261 | aroAdel His⁻ | $10^6$ | 4/4 | 4/5 |
| CS322 | aroA⁻ PhoP$^c$ | $10^6$ | 5/5 | |
| CS323 | SL3261 PhoP$^c$ | $10^6$ | 5/5 | |
| CS322 | aroA⁻ PhoP$^c$ | $10^7$ | 5/5 | |
| CS323 | SL3261 PhoP$^c$ | $10^7$ | 5/5 | |
| CS322 | aroA⁻ PhoP$^c$ | $10^8$ | | 5/5 |
| CS323 | SL3261 PhoP$^c$ | $10^8$ | | 5/5 |
| CS315 | aroA⁻ PhoP⁻ | | 5/5 | |
| CS316 | SI3261 PhoP⁻ | $10^8$ | 5/5 | |

(*) Ratio of survivors to number of mice challenged.
(**) Indicates oral inoculation all other experiments were intraperitoneal inoculation.
CS004 = aroA554::rn10.
SL3261 = aroADEL407 hisG46.
CS322 = aroA554::Tn10 pho-24.
CS323 = aroADEL407 pho-24.
CS315 = aroA554::Tn10 phoP102::Tn10d-Cam.
CS316 = aroADEL407 hisG46 phoP102::Tn10d-Cam.
CS026 = pagC1::TnphoA pho-24 phoN2 zxx::6251TN10d-Cam.

Salmonella typhi phoP Regulon Mutations

The phoP regulon is at least partially conserved in *S. typhi* DNA hybridization studies as well as P22 bacteriophage transductional crosses have documented that the phoP, phoQ, and pagC genes appear highly conserved between *S. typhi* and *S. typhimurium* mutations in these genes in *S. typhi* have been made.

Salmonella Live Vaccines as Delivery Systems for Heterologous Antigens.

The vector used in the vaccine delivery system is a derivative of pJM703.1 described in Miller et al., 1988, J. Bact. 170:2575, hereby incorporated by reference. This vector is an R6K derivative with a deletion in the pir gene. R6K derivatives require the protein product of the pir gene to replicate. *E. coli* that contain the pir gene present as a lambda bacteriophage prophage can support the replication of this vector. Cells that do not contain the pir gene will not support the replication of the vector as a plasmid. This vector also contains the mob region of RP4 which will allow mobilization into other gram negative bacteria by mating from *E. coli* strains such as SM101lambda pir, which can provide the mobilization function in trans.

Figure 2:
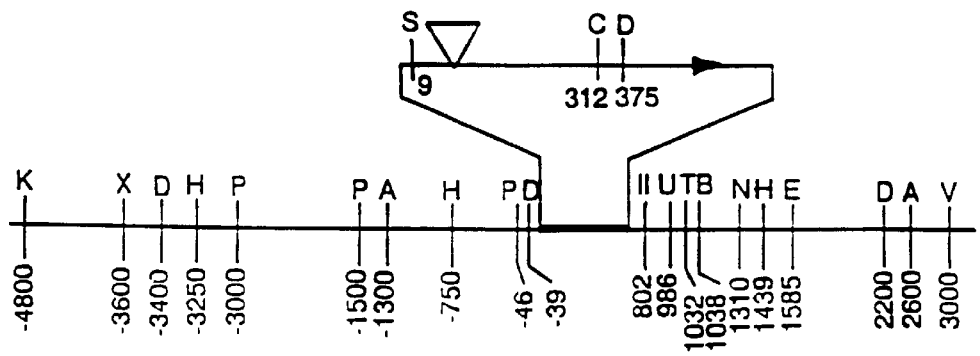
FIG. 2 is a map of the restriction endonuclease sites of the pagC locus.

The pagC region is shown in FIGS. 2 and 3. FIG. 2 shows the restriction endonuclease sites of the pagC locus. The heavy bar indicates pagC coding sequence. The TnphoA insertion is indicated by an inverted triangle. The direction of transcription is indicated by the arrow and is left to right. The numbers indicate the location of endonuclease sites, in number of base pairs, relative to the start codon of predicted pagC translation with positive numbers indicating location downstream of the start codon and negative numbers indicating location upstream of the start codon. A is AccI, B is BglI, C is ClaI, D is DraI, E is EcoRI, H is HpaI, N is NruI, P is PstI, S is SspI, T is StuI, U is PvuII, V is EcoRV, and II is BglII. FIG. 3 shows the DNA sequence (Sequence I.D. No. 1) and translation of pagC::TnphoA. (SEQ ID NO: 5). The heavy underlined sequence indicates a potential ribosomal binding site. The single and double light underlines indicate sequences in which primers were constructed complementary to these nucleotides for primer extension of RNA analysis. The asterisk indicates the approximate start of transcription. The arrow indicates the direction of transcription. The boxed sequences indicate a region that may function in polymerase binding and recognition. The inverted triangle is the site of the sequenced TnphoA insertion junction. The arrow indicates a potential site for single sequence cleavage.

3 kilobases of DNA containing the pagC gene (from the PstI restriction endonuclease site 1500 nucleotides 5' to the start of pagC translation to the EcoRI restriction endonuclease site 1585 nucleotides downstream of pagC translation termination) were inserted into the pJM703.1 derivative discussed above. The pagC sequence from the ClaI restriction endonuclease site was deleted (490 nucleotides) and replaced with a synthetic oligonucleotide polylinker that creates unique restriction endonuclease sites. DNA encoding one or more heterologous proteins, e.g., an antigen, can be inserted into this site. This creates a vector which allows the insertion of multiple foreign genes into the DNA surrounding pagC.

The vector can be mobilized into Salmonella by mating or any other delivery system, e.g., heat shock, bacteriophage transduction or electroporation. Since it can not replicate, the vector can only insert into Salmonella by site specific recombination with the homologous DNA on both sides of the pagC gene. This will disrupt and inactivate the native pagC locus and replace it with the disrupted pagC DNA carried on the vector.

Such recombination events can be identified by marker exchange and selective media if the foreign DNA inserted into the pagC locus confers a growth advantage. The insertion of antibiotic resistance genes for selection is less desirable as this could allow an increase in antibiotic resistance in the natural population of bacteria. Genes which confer resistance to substances other than antibiotics e.g., to heavy metals or arsenic (for mercury resistance, see Nucifora et al., 1989, J. Bact., 171:4241–4247, hereby incorporated by reference), can be used to identify transformants. Alternatively, selection can be performed using a Salmonella recipient strain that carries an auxotrophic mutation in a metabolic pathway and a vector that carries DNA that complements the auxotrophic mutation. Many Salmonella live vaccine prototypes contain mutations in histidine or purine pathways thus complementation of these metabolic auxotrophies can be used to select for integrants. (Purine mutations specifically have been shown to be too attenuated for use in man.) Further proof of marker exchange can be documented by loss of the ampicillin resistance (carried on the plasmid backbone) or by blot hybridization analysis.

A gene useful for selection can be cloned by complementation of a vaccine strain with a metabolic auxotrophy. Specific examples include the cloning of the DNA encoding both purB and phoP by complementation of a strain deleted for function of both these genes. Salmonella gene libraries have been constructed in a pLAFR cosmid vector (Frindberg et al., 1984, Anal. Biochem. 137:266–267, hereby incorporated by reference) by methods known to those skilled in the art. pLAFR cosmids are broad host range plasmids which can be mobilized into Salmonella from *E. coli*. An entire bank of such strains can be mobilized into Salmonella vaccine strains and selected for complementation of an auxotrophic defect (e.g., in the case of purB growth on media without adenine). The DNA able to complement this defect is then identified and can be cloned into the antigen delivery vector.

As discussed above heterologous genes can be inserted into the polylinker that is inserted into the pagC sequence of the vector. The heterologous genes can be under the control of any of numerous environmentally regulated promotor systems which can be expressed in the host and shut off in the laboratory. Because the expression of foreign proteins, especially membrane proteins (as are most important antigens), is frequently toxic to the bacterium, the use of environmentally regulated promoters that would be expressed in mammalian tissues at high levels but which could be grown in the laboratory without expression of heterologous antigens would be very desirable. Additionally, high expression of antigens in host tissues may result in increased attenuation of the organism by diverting the metabolic fuel of the organism to the synthesis of heterologous proteins. If foreign antigens are specifically expressed in host phagocytic cells this may increase the immune response to these proteins as these are the cells responsible for processing antigens.

The promoter systems likely to be useful include those nutritionally regulated promoter systems for which it has been demonstrated that a specific nutrient is not available to bacteria in mammalian hosts. Purines, Sigwart et al.,.1989, Infect. Immun., 57:1858 and iron, Finklestein et al., 1983, Rev. Infect. Dis. 5:S759, e.g., are not available within the host. Promoters that are iron regulated, such as the aerobactin gene promoter, as well as promoters for biosynthetic genes in purine pathways, are thus excellent candidates for testing as promoters that can be shut down by growth in high concentrations of these nutrients. Other useful environmentally regulated Salmonella promoters include promoters for genes which encode proteins which are specifically expressed within macrophages, e.g., the DnaK and GroEL proteins, which are increased by growth at high temperature, as well as some phoP activated gene products, Buchmeier et al., 1990, Science 248:730, hereby incorporated by reference. Therefore, promoters such as the pagC 5' controlling sequences and the better characterized promoters for heat shock genes, e.g., GroEL and DnaK, will be expected to be activated specifically within the macrophage. The macrophage is the site of antigen processing and the expression of heat shock genes in macrophages and the wide conservation of heat shock genes in nature may explain the immunodominance of these proteins. A consensus heat shock promoter sequence is known and can be used in the vectors (Cowling et al., 1985, Proc. Natl. Acad. Sci. U.S.A. 82:2679, hereby incorporated by reference).

The vectors can include an environmentally regulated T7 polymerase amplification system to express heterologous proteins. For example, the T7 polymerase gene (cloned by Stan Tabor and Charles Richardson, See Current Protocols in Molecular Biology ed. Ausubel et al., 1989, (page 3.5.1.2) John Wiley and Sons, hereby incorporated by reference) under control of an iron regulated promoter, can be included on the vectors described above. We have inserted the aerobactin gene promoter of E. coli with the sequence CATTTCTCATTGATAATGAGAATCAT-TATTGACATAATTGTTATTATTTTACG (SEQ ID NO:2), Delorenzo et al. J. Bact. 169:2624, hereby incorporated by reference, in front of the T7 polymerase gene and demonstrated iron regulation of the gene product. This version of the vector will also include one or more heterologous antigens under the control of T7 polymerase promoters. It is well known that RNA can be synthesized from synthetic oligonucleotide T7 promoters and purified T7 in vitro. When the organism encounters low iron T7 polymerase will be synthesized and high expression of genes with T7 promoters will be facilitated.

The pagC gene and pagC Gene Product.

Strains, materials, and methods. The following strains, materials, and methods were used in the cloning of pagC and in the analysis of the gene and its gene product.

Rich media was Luria broth (LB) and minimal media was M9, Davis et al., 1980, supra. The construction of S. typhimurium strain CS119 pagC1::TnphoA phoN2 zxx::6251 Tn10d-Cam was previously described, Miller et al., 1989, supra. American Type Culture Collection (ATCC) S. typhimurium strain 10428 included CS018 which is isogenic to CS119 except for phoP105::Tn10d, Miller et al., 1989, supra, CS022 pho-24, Miller et al., 1990, J. Bacteriol. 172:2485–2490, hereby incorporated by reference, and CS015 phoP102::Tn10d-cam, Miller et al., 1989, supra. Other wild type strains used for preparation of chromosomal DNA included S. typhimurium LT2 (ATCC 15277), S. typhimurium Q1 and S. drypool (Dr. J. Peterson U. Texas Medical Branch, Galveston), and Salmonella typhi Ty2 (Dr. Caroline Hardegree, Food and Drug Administration). pLAFR cosmids were mobilized from E. coli to S. typhimurium using the E. coli strain MM294 containing pRK2013, Friedman et al., 1982, Gene 18:289–296, hereby incorporated by reference. Alkaline phosphatase (AP) activity was screened on solid media using the chromogenic phosphatase substrate 5-bromo-4-chloro-3-indolyl phosphate (XP). AP assays were performed as previously described, Brickman et al., 1975, J. Mol. Biol. 96:307–316, hereby incorporated by reference, and are reported in units as defined by Miller, Miller, 1972, supra, pp. 352–355.

One dimensional protein gel electrophoresis was performed by the method of Laemmli, 1970, Nature, 227:680–685, hereby incorporated by reference, and blot hybridization using antibody to AP was performed as previously described, Peterson et al., 1988, Infect. Immun. 56:2822–2829, hereby incorporated by reference. Whole cell protein extracts were prepared, from saturated cultures grown in LB at 37° C. with aeration, by boiling the cells in SDS-pagE sample buffer, Laemmli, 1970, supra. Two dimensional gel electrophoresis was performed by the method of O'Farrell, 1975, J. Biol. Chem. 250:4007, hereby incorporated by reference. Proteins in the 10% polyacrylamide slab gels were visualized by silver staining, Merril et al., 1984, Methods in Enzymology, 104:441, hereby incorporated by reference.

Chromosomal DNA was prepared by the method of Mekalanos, 1983, Cell, 35:253–263, hereby incorporated by reference. DNA, size fractionated in agarose gels, was transferred to nitrocellulose (for blot hybridization) by the method of Southern, 1975, J. Mol. Biol. 98:503–517, hereby incorporated by reference. DNA probes for Southern hybridization analysis were radiolabeled by the random primer method, Frinberg et al., 1984, supra. Plasmid DNA was transformed into E. coli and Salmonella by calcium chloride and heart shock, Mekalanos, 1983, supra, or by electroporation using a Genepulser apparatus (Biorad, Richmond, Calif.) as recommended by the manufacturer, Dower et al., 1988, Nucl. Acids Res. 16:6127–6145, hereby incorporated by reference. DNA sequencing was performed by the dideoxy chain termination method of Sanger et al., 1977, Proc. Natl. Acad. Sci. U.S.A., 74:5463–5467, hereby incorporated by reference, as modified for use with SEQUENASE® (U.S. Biochemical, Cleveland, Ohio). Oligonucleotides were synthesized on an Applied Biosystems Machine and used as primers for sequencing reactions and primer extension of RNA. Specific primers unique to the two ends of TnphoA, one of which corresponds to the alkaline phosphatase coding sequence and the other to the right IS50 sequence, were used to sequence the junctions of the transposon insertion.

Construction of a S. typhimurium cosmid gene bank in pLAFR3 and screening for clones containing the wild type pagC DNA was performed as follows. DNA from *S. typhimurium* strain ATCC 10428 was partially digested using the restriction endonuclease Sau3A and then size selected on 10–40% sucrose density gradient. T4 DNA ligase was used to ligate chromosomal DNA of size 20–30 kilobases into the cosmid vector pLAFR3, a derivative of pLAFR1, Friedman et al., 1982, Gene 18:289–296, hereby incorporated by reference, that was digested with the restriction endonuclease BamHI. Cosmid DNA was packaged and transfected into *E. coli* strain DH5-α using extracts purchased from Stratagene, La Jolla, Calif. Colonies were screened by blot hybridization analysis.

The analysis of proteins produced from cloned DNA by in vitro transcription/translation assays was analyzed as follows. These assays were performed with cell free extracts, (Amersham, Arlington Heights, Ill.), and were performed using conditions as described by the manufacturer. The resultant radiolabeled proteins were analyzed by SDS-pagE.

RNA was purified from early log and stationary phase Salmonella cultures by the hot phenol method, Case et al., 1988, Gene 72:219–236, hereby incorporated by reference, and run in agarose-formaldehyde gels for blot hybridization analysis, Thomas, 1980, Proc. Natl. Acad. Sci. U.S.A. 77:5201, hereby incorporated by reference. Primer extension analysis of RNA was performed as previously described, Miller et al., 1986, Nuc. Acids. Res. 14:7341–7360, hereby incorporated by reference, using AMV reverse transcriptase (Promega, Madison, Wis.) and synthesized oligonucleotide primers complementary to nucleotides 335–350 and 550–565 of the pagC locus.

Identification of an 18 kDa protein missing in a pagC mutant of *S. typhimurium*pagC mutant strain CS119 was analyzed by two dimensional protein electrophoresis to detect protein species that might be absent as a result of the TnphoA insertion. Only a single missing protein species, of approximately 18 kD and pI-8.0, was observed when strains, isogenic except for their transposon insertions, were subjected to this analysis. This 18 kDa species was also missing in similar analysis of Salmonella strains with mutations phoP and phoQ. Though two-dimensional protein gel analysis might not detect subtle changes of protein expression in strain CS119, this suggested that a single major protein species was absent as a result of the pagC::TnphoA insertion.

Additional examination of the 2-dimensional gel analysis revealed a new protein species of about 45 kDa that is likely the pagC-Ap fusion protein. The pagC-AP fusion protein was also analyzed by Western blot analysis using antisera to AP and found to be similar in size to native AP (45 kDa) and not expressed in PhoP-*S. typhimurium*.

Cloning of the pagC::TnphoA insertion Chromosomal DNA was prepared from *S. typhimurium* strain CS119 and a rough physical map of the restriction endonuclease sites in the region of the pagC::TnphoA fusion was determined by using a DNA fragment of TnphoA as a probe in blot hybridization analysis. This work indicated that digestion with the restriction endonuclease ecoRV yielded a single DNA fragment that included the pagC::TnphoA insertion in addition-to several kilobases of flanking DNA. Chromosomal DNA from strain CS119 was digested with EcoRV (blunt end) and ligated into the bacterial plasmid vector pUC19 (New England Biolabs) that had been digested with the restriction endonuclease SmaI (blunt end). This DNA was electroporated into the *E. coli* strain DH5-α (BRL) and colonies were plated onto LB agar containing the antibiotics kanamycin (TnphoA encoded and ampicillin (pUC19 encoded). A single ampicillin and kanamycin resistant clone containing a plasmid designated pSM100 was selected for further study.

A radiolabeled DNA probe from pSM100 was constructed and used in Southern hybridization analysis of strain CS119and its wild type parent ATCC 10428 to prove that the pagC::TnphoA fusion had been cloned. The probe contained sequences immediately adjacent to the transposon at the opposite end of the alkaline phosphatase gene [HpaI endonuclease generated DNA fragment that included 186 bases of the right IS50 of the transposon and 1278 bases of Salmonella DNA (FIG. 2). As expected, the pSM100 derived probe hybridized to an 11–12 kb AccI endonuclease digested DNA fragment from the strain containing the transposon insertion, CS119. This was approximately 7.7 kb (size of TnphoA) larger than the 3.9 kB AccI fragment present in the wild type strain that hybridizes to the probe. In addition, a derivative of plasmid pSM100, pSM101 (which did not allow expression of the pagC-PhoA gene fusion off the lac promoter), was transformed into phoP- (strain Cs015) and phoN- (strain CS019) Salmonella strains and the cloned AP activity was found to be dependent on phoP for expression. Therefore we concluded that the cloned DNA contained the pagC::TnphoA fusion.

The presence of the pagC gene was also demonstrated in other strains of *S. typhimurium*, as well as in *S. typhi*, and *S. drypool*. All Salmonella strains examined demonstrated similar strong hybridization to an 8.0 kb EcoRV and a 3.9 kb AcciI restriction endonuclease fragment suggesting that pagC is a virulence gene common to Salmonella species.

The pagC gene probe from nucleotides −46 (with 1 as the first base of the methionine to 802 (PstI site to the BglII site) failed to cross hybridize to DNA from *Citrobacter freundii*, *Shigella flexneri*, *Shigella sonnei*, *Shigella dysenterial*, *Escherichia coli*, *Vibrio cholerae*, *Vibrio vulnificus*, *Yersenia entero colitica*, and *Klebsiella pneumonia*.

Cloning of the wild type pagC locus DNA and its complementation of the virulence defect of a *S. typhimurium* pagC mutant. The same restriction endonuclease fragment described above was used to screen a cosmid gene bank of wild type strain ATCC 10428. A single clone, designated pWP061, contained 18 kilobases of *S. typhimurium* DNA and hybridized strongly to the pagC DNA probe. pWP061 was found to contain Salmonella DNA identical to that of pSM100 when analyzed by restriction endonuclease analysis and DNA blot hybridization studies. Probes derived from pWP061 were also used in blot hybridization analysis with DNA from wild type and CS119 *S. typhimurium*. Identical hybridization patterns were observed to those seen with pSM100. pWP061 was also mobilized into strain CS119, a pagC mutant strain. The resulting strain had wild type virulence for BALB/c mice (a $LD_{50}$ less than 20 organisms when administered by IP injection). Therefore the cloned DNA complements the virulence defect of a pagC mutant strain.

Since, a wild type cosmid containing pagC locus DNA was found to complement the virulence defect of a pagC mutant *S. typhimurium* strain, it was concluded that the pagC protein is an 188 amino acid (18 kDa) membrane (see below) protein essential for survival within macrophages and virulence of *S. typhimurium*.

Physical mapping of restriction endonuclease sites, DNA sequencing, and determination of the pagC gene product. Restriction endonuclease analysis of plasmid pSM100 and pWP061 was performed to obtain a physical map of the pagC locus, and, in the case of PSM100, to determine the direction of transcription (FIG. 2). DNA subclones were generated and the TnphoA fusion junctions were sequenced, as well as the Salmonella DNA extending from the HpaI site, 828 nucleotides 5' to the phoA fusion junction, to the EcoRI site 1032 nucleotides 3' to the TnphoA insertion (FIGS. 2 and 3). The correct reading frame of the DNA sequence was deduced from that required to synthesize an active AP gene fusion. The deduced amino acid sequence of this open reading frame was predicted to encode a 188 amino acid protein with a predicted pI+8.2. This data were consistent with the 2-D polyacrylamide gel analysis of strain CS119 in which an 18 kDa protein of approximate pI+8.0 was absent. No other open reading frames, predicted to encode peptides larger than 30 amino acids, were found.

The deduced amino acid sequence (SEQ ID NO:5) of the 188 amino acid open reading frame contains a methionine start codon 33 amino acids from the fusion of pagC and AP (FIG. 3). This 33 amino acid pagC contribution to the fusion protein was consistent with the size observed in Western blot analysis and contains a hydrophobic N-terminal region, identified by the method of Kyle et al., 1982, J. Mol. Biol. 157:105–132, hereby incorporated by reference, that is a typical bacterial signal sequence, Von Heinje, 1985, J. Mol. Biol. 184:99–105, hereby incorporated by reference. Specifically, amino acid 2 is a positively charged lysine, followed by a hydrophobic domain and amino acid 24 is a negatively charged aspartate residue. A consensus cleavage site for this leader peptide is predicted to be at an alanine residue at amino acid 23, Von Heinje, 1984, J. Mol. Biol. 173:243–251, hereby incorporated by reference. The DNA sequence also revealed a typical ribosomal binding site, Shine et al., 1974, Proc. Natl. Acad. Sci. U.S.A. 71:1342–1346, hereby incorporated by reference, at 6-2 nucleotides 5' to the predicted start of translation (FIG. 3) nucleotides 717–723). This suggested that the open reading frame was, in fact, translated and further supported the assumption that this was the deduced amino acid sequence of the pagC protein interrupted by the TnphoA insertion (FIG. 3).

In vitro synthesis of proteins by the cloned pagC locus. To detect if other proteins were encoded by pagC and to determine the approximate size of the pagC gene product, an in vitro coupled transcription/translation analysis was performed. A 5.3 kilobase EcoRI fragment of pWP061 was inserted into pUC19 so that the pagC gene would not be expressed off the lac promotor. This plasmid was used in an in vitro coupled transcription-translation assay. A single protein of approximately 22 kilodaltons was synthesized by the cell free system. The size was compatible with this being the precursor of the pagC protein containing its leader peptide. These data further support the conclusion the single and the single pagC gene product had been identified.

Identification of the pagC encoded RNA. An approximately 1100 nucleotide RNA is encoded by pagC. The pagC gene is highly expressed by cells with a phoP constitutive phenotype of pag activation, as compared to wild type and phoP constitutive phenotype of pag activation, as compared to wild type and phoP⁻ bacteria. In these blot hybridization experiments pagC is only detected in wild type cells grown in rich media during stationary growth. This result, coupled with previous work, Miller et al., 1989, supra, Miller et al., 1990, supra, demonstrates that pagC is transcriptionally regulated by the phoP gene products and is only expressed during early logarithmic phase growth in rich media by cells with a phoP constitutive phenotype.

The size of the pagC transcript is approximately 500 nucleotides greater than that necessary to encode the 188 amino acid protein. Primer extension analysis of Salmonella RNA using oligonucleotide primers specific for pagC sequence was performed to determine the approximate start site of transcription and to determine whether these nucleotides might be transcribed 5' or 3' to the 188 amino acid pagC gene product. Primer extension analysis with an oligonucleotide predicted to be complementary to nucleotides 550–565 of pagC, 150 nucleotides 5' to the predicted start codon, resulted in an approximately 300 nucleotide primer extension product. Therefore a primer further upstream was constructed complementary to nucleotides 335–350 of pagC and used in a similar analysis. A primer extension product of 180 nucleotides was observed to be primer specific. This is consistent with transcription starting at nucleotide 170 (FIG. 3). Upstream of the predicted transcriptional start, at nucleotides 153–160, a classic RNA polymerase binding site was observed with the sequence TATAAT at −12 nucleotides as well as the sequence TAATAT at −10 nucleotides. No complete matches were observed for the consensus RNA polymerase recognition site (TTGACA) 15–21 nucleotides upstream from the −10 region. AT −39 (126–131) nucleotides (TTGGAA), −38 (127–132) nucleotides (TTGTGG), and −25 (135–140) nucleotides (TTGATT) are sequences that have matches with the most frequently conserved nucleotides of this sequence.

Based on the above results transcription was predicted to terminate near the translational stop codon of the 188 amino acid protein (nucleotide 1295, FIG. 3). Indeed, a stem loop configuration was found at nucleotides 1309–1330 that may function as a transcription terminator. This was consistent with the lack of evidence of open reading frames downstream of the 188 amino acid protein and the lack of synthesis of other transcription/translation using the cloned pagC DNA. This further suggests that the pagC::TnphoA insertion inactivated the synthesis of only a single protein.

Similarity of pagC to Ail and Lom. A computer analysis of protein similarity using the National Biomedical Research Foundation/Protein Identification Resource, George et al., 1986, Nucleic Acids Res. 14:11–15, hereby incorporated by reference, protein sequence base was conducted to identify other proteins that had similarity to pagC in an attempt to find clues to the molecular function of this protein. Remarkably, pagC was found to be similar to a bacteriophage lambda protein, Lom, that has been localized to the outer membrane in minicell analysis, Court et al., 1983, Lambda II, Hendrix, R. W. et al. ed. Cold Spring Harbor Laboratory (Cold Spring Harbor N.Y.), pp. 251–277, hereby incorporated by reference, and demonstrated to be expressed by lambda lysogens of *E. coli*, Barondess, et al., 1990, Nature 346:871–874, hereby incorporated by reference. Recently, the deduced amino acid sequence of the cloned ail gene product of *Y. enterocolitica* was determined and found to also be similar to Lom, Miller et al., 1990b, J. Bacteriol. 172:1062–1069. Therefore, a protein family sequence alignment was performed using a computer algorithm that establishes protein sequence families and consensus sequences, Smith et al., 1990, Proc. Natl. Acad. Sci. 87:118–122, hereby incorporated by reference. The formation of this family is indicated by the internal data base values of similarity between these proteins : pagC and Lom (107.8), pagC and Ail (104.7), and Ail and Lom (89.8). These same proteins were searched against 314 control sequences in the data base and mean values and ranges were 39.3 (7.3–52.9) pagC, 37.4 (7.3–52.9) Ail, and 42.1 (7.0–61.9) Lom. The similarity values for this protein family are all greater than 3.5 standard deviations above the highest score obtained for similarity to the 314 random sequences. No other similarities or other family members were found in the database. Regions of similarity are located not only in the leader peptide transmembrane domains but throughout the protein.

pagC Mutant Strains Are Attenuated For Virulence.

*Salmonella typhimurium* strains of the invention with a pagC mutation were attenuated for virulence by least 1,000-fold.

prg genes

As discussed above, phoP/phoQ constitutive mutations (phenotype PhoP$^c$) increase the expression of pags and repress the synthesis of approximately 20 proteins encoded by phoP-repressed genes (prgs). PhoP$^c$ bacteria are attenutated for mouse virulence suggesting that prgs are virulence genes.

By use of the transposon, TnphoA, five unlinked prg loci were identified. In general, media conditions (starvation) that activate pag expression repress prg expression. One prg locus, prgH, was demonstrated to contribute to mouse virulence by both the oral and the intraperitoneal route. Both PrgH as well as PhoP$^c$ mutant *S. typhimurium* were found to be defective in induction of endocytosis by epithelial cells. Identification and mutation of such virulence genes will be useful in vaccine development.

Strains, materials and methods.

All bacterial strains used in the characterization of prg genes are listed in Table 5.

TABLE 5

| Strain | Relevant genotype or description | Reference or source |
|---|---|---|
| | *S. typhimurium* 14028s derivatives | |
| 14028s | Wild type | ATCC |
| CS002 | phoP12 | This work |
| CS003 | ΔphoP ΔpurB | This work |
| CS012 | pagA1::Mu dJ | This work |
| CS013 | pagB1::Mu dJ | This work |
| CS119 | pagC1::TnphoA phoN2 zxx::6251 Tn10d-Cm | This work |
| CS015 | phoP-102::Tn10d-Cm | This work |
| CS019 | phoN2 zxx::6251Tn10d-Cm | This work |
| CS022 | pho-24 | This work |
| CS023 | pho-24 phoN2 zxx::6251Tn10d-Cm | This work |
| CS030 | phoN2 zxx::6251Tn10d-Cm phoP12 | This work |
| AD154 | phoP12 purB1744::Tn10 | Gift of E. Eisenstadt |
| CS031 | pho-24 purB1744::Tn10 | This work |
| IB001 | phoN2 zxx::6251Tn10d-Cm ΔphoP ΔpurB | This work |
| IB002 | CS030 with prgA1::TnphoA | This work |
| IB003 | IB002 with pho-24 purB1744::Tn10 | This work |
| IB004 | IB002 with phoP12 purB1744::Tn10 | This work |
| IB005 | CS019 with prgA1::TnphoA | This work |
| IB006 | CS015 with prgA1::TnphoA | This work |
| IB007 | CS030 with prgB1::TnphoA | This work |
| IB008 | IB007 with pho-24 purB1744::Tn10 | This work |
| IB009 | IB007 with phoP12 purB1744::Tn10 | This work |
| IB010 | CS019 with prgB1::TnphoA | This work |
| IB011 | CS015 with prgB1::TnphoA | This work |
| IB012 | CS030 with prgB2::TnphoA | This work |
| IB013 | IB012 with pho-24 purB1744::Tn10 | This work |
| IB014 | IB012 with phoP12 purB1744::Tn10 | This work |
| IB015 | CS019 with prgB2::TnphoA | This work |
| IB016 | CS015 with prgB2::TnphoA | This work |
| IB017 | CS030 with prgC1::TnphoA | This work |
| IB018 | IB017 with pho-24 purB1744::Tn10 | This work |
| IB019 | IB017 with phoP12 purB1744::Tn10 | This work |
| IB020 | CS019 with prgC1::TnphoA | This work |
| IB021 | CS015 with prgC1::TnphoA | This work |
| IB022 | CS030 with prgE1::TnphoA | This work |
| IB023 | IB022 with pho-24 purB1744::Tn10 | This work |
| IB024 | IB022 with phoP12 purB1744::Tn10 | This work |
| IB025 | CS019 with prgE1::TnphoA | This work |
| IB026 | CS015 with prgE1::TnphoA | This work |
| IB027 | CS030 with prgE2::TnphoA | This work |
| IB028 | IB027 with pho-24 purB1744::Tn10 | This work |
| IB029 | IB027 with phoP12 purB1744::Tn10 | This work |
| IB030 | CS019 with prgE2::TnphoA | This work |
| IB031 | CS015 with prgE2::TnphoA | This work |
| IB032 | CS030 with prgE3::TnphoA | This work |
| IB033 | IB032 with pho-24 purB1744::Tn10 | This work |
| IB034 | IB032 with phoP12 purB1744::Tn10 | This work |
| IB035 | CS019 with prgE3::TnphoA | This work |
| IB036 | CS015 with prgE3::TnphoA | This work |
| IB037 | IB001 with prgH1::TnphoA | This work |
| IB038 | IB037 with pho-24 purB1744::Tn10 | This work |
| IB039 | IB037 with phoP12 purB1744::Tn10 | This work |
| IB040 | CS019 with prgH1::TnphoA | This work |
| IB041 | CS015 with prgH1::TnphoA | This work |
| IB042 | Tn5B50-380 in IB040 | This work |
| IB043 | pWKSH5 in IB040 | This work |
| IB044 | pWKSH5 in CS022 | This work |

TABLE 5-continued

| Strain | Relevant genotype or description | Reference or source |
|---|---|---|
| CS032 | oxiA1049::Mu d1-8 supD10 | This work |
| CS033 | oxiC1048::Mu d1-8 supD10 | This work |
| CS034 | oxiE4::Mu d1 ΔnadA100 | This work |
| Other S. typhimurium derivatives | | |
| AK3011-AK3314 | Collection of randomly spaced Tn10Δ16Δ17 insertions | (19) |
| TT520 | sr1-202::Tn10 | (41) |
| TT2979 | sr1-211::Tn5 | (41) |
| TN3061 | zcf-845::Tn10 dcp-1 zhg-1635::Tn10dCm | (41) |
| SH7782 | ompD::Tn5 | (41) |
| $_x$4115 | invA::cat | (13) |
| EE517 | Δhil-517 (Tn5B50-380) | Gift of C. Lee |
| JF897 | oxiA1049::Mu d1-8 supD10 | (2) |
| JF896 | oxiC1048::Mu d1-8 supD10 | (2) |
| JF739 | oxiE4::Mu d1 ΔnadA100 | (2) |
| S. enteritidis | | |
| CDC5 | clinical wild-type isolate | (45) |
| SM7 | Str$^r$ smb | (45) |
| E. coli | | |
| SM10(pRT291) | contains plasmid pRT291 (TnphoA) derived from pRK290 selecting for Tc$^r$ and Km$^r$. | (49) |
| MM294(pPH1JI) | contains Gm$^r$ plasmid pPH1JI, which is incompatible with pRK290 | (49) |
| VV42(pWKSH5) | contains plasmid pWKSH5, a derivative of pSC101 that contains a 5.1 kb HindIII fragment of hil DNA including prgH V. Bajaj and C. Lee | (51) |

(19) Kukral et al., Journal of Bacteriology, 169:1787–1793, 1987
(41) Sanderson et al., Microbiological Reviews, 52:485–532, 1988
(13) Galan et al., Infection and Immunity, 59:3116–3121, 1990
(2) Aliabadi et al., Journal of Bacteriology, 165:780–786, 1986
(45) Stone et al., Journal of Bacteriology, 174:3945–3952, 1992

Bacteria were grown as follows: Luria-Bertani (LB) broth was used as rich medium. Antibiotics were used in the following concentrations in growth media or agar: ampicillin 100 μg/ml (Ap), chloramphenicol 25 μg/ml (Cm), gentamicin 30 μg/ml (Gm), kanamycin 45 μg/ml (Km), and tetracycline 25 μg/ml (Tc). The chromogenic substrate 5-bromo-4-chloro-3-indolyl-phosphate (p-toluidine salt) (XP) was used to detect phosphatase activity/on agar at a final concentration of 40 μg/ml. p-nitrophenyl phosphate (p-NPP) was used as a substrate for quantitative measurement of alkaline phosphatase activity. Media was buffered to various pH ranges with 1M sodium citrate. E media (Vogel-Bonner minimal) was prepared as described by Davis et al., 1980, Advanced Bacterial Genetics: A Manual for Genetic Engineering. Cold Spring Harbor Laboratory, Cold Spring Harbor, N.Y. Nitrogen-, carbon-, and phosphate free medium (N$^-$C$^-$P$^-$) was prepared as described by Kier et. al., 1977, J. Bacteriol. 130:399, herein incorporated by reference. This starvation medium was supplemented with 0.04% (wt/vol) glucose as the carbon source, 10 mM NH$_4$Cl as the nitrogen source, and 1 mM NaH$_2$PO$_4$.H$_2$O as the phosphate source. The carbon concentration is one log less than described by Kier et al., supra.

Alkaline phosphatase (AP) activity of strains isogenic except for mutations in the phoP locus was measured in cultures grown from a single colony inoculum under various oxygen tensions with or without shaking at 37° C. Anaerobic cultures were grown in an anaerobic chamber (Coy Laboratories Products, Inc.) with a gas mixture of 80% N$_2$, 10% O$_2$, and 10% CO$_2$ at 37° C. For acid regulation, aliquots of mid-logarithmic cultures were removed to measure initial pH and AP activity. 1M sodium citrate (pH>6.0) or 1M citric acid (pH 4.7) were added to equivalent amounts of culture to a final concentration of 50 mM citrate. Cultures were grown aerobically for two hours at 37° C. and then pH and AP measurements were taken. AP activity was measured as described previously (Michaelis et al., 1983, J. Bacteriol. 154:366–374, herein incorporated by reference). AP units were calculated by the following formula: units={OD$_{420}$/[time (minutes)×volume×OD$_{600}$]}×1000 as defined by Miller for β-galactosidase (Miller et al., 1972, Experiments in molecular genetics, p. 352–355. Cold Spring Harbor Laboratory, Cold Spring Harbor, N.Y.).

Standard bacterial genetic techniques were used to study prg loci. Bacteriophage P22HTint-mediated transduction was performed as according to methods known in the art. TnphoA mutagenesis was performed using a broad host range plasmid (pRT291) to deliver TnphoA (Taylor et al., 1989, J. Bacteriol. 171:1870, herein incorporated by reference). Transpositions of TnphoA into Salmonella DNA were identified by use of the incompatibility plasmid pPH1JI (Taylor et al., supra). Screening for phoP-repressed genes was performed using CS031, the donor strain of the pho-24 allele. CS031 was constructed by a P22 bacteriophage transductional cross between strains AD154 and CS022 which contains the purB::Tn10 allele and the pho-24 allele, respectively. The linkage of pho-24 and purB::Tn10 was 70%, similar to the linkage of purB to other phoP alleles. Therefore, when P22 bacteriophage transductional crosses were performed between CS031 and the strains containing active gene fusions to phoA, strains could be screened for loss of fusion protein activity on acquisition of tetracycline resistance. Initial screening involved detection of loss of AP activity in approximately 70% of colonies that acquired tetracycline resistance, as they were presumed to contain the pho-24 allele. In addition, controls were performed using strain AD154 that contains the same purB::Tn10 allele linked to a phoP null allele, phoP12. Plasmid DNA was transformed into *S. typhimurium* strain LB5010 by the calcium chloride and heat shock procedure (Maclachlan et al., 1985, J. Bacteriol. 161:442).

Isolation of strains with TnphoA insertions in phoP-repressed genes.

Constitutive mutations in the phoP locus (phenotype PhoP$^c$) that result in increased expression of pags in an unregulated fashion also markedly attenuate *S. typhimurium* virulence and survival within macrophages. The virulence defect of PhoP$^c$ strains can be explained by their decreased expression of approximately 20 polypeptides encoded by phoP-repressed genes (prgs).

A PhoP⁻PhoN⁻ strain (IB001) was constructed by a P22 transductional cross between CS019 and CS003. IB001 was then mutagenized with TnphoA (so that background acid phosphatase, encoded by phoN, would not interfere with the measurement of fusion protein activity on alteration of the phoP locus) and 1800 individual blue colonies with PhoA fusion protein activity were isolated on LB agar plates containing XP. These colonies were the result of 18 separate matings with approximately 20 pools in each. These strains were tested for reduction of fusion protein activity on acquisition of the pho-24 allele (CS031), which resulted in a PhoP$^c$ phenotype. AP assays were then performed on strains isogenic except for the phoP locus.

The PhoP$^c$ phenotype was confirmed in these strains by preparation of whole cell protein extracts and SDS-PAGE analysis. All strains with a PhoP$^c$ phenotype demonstrated the expected distinctive pattern of protein expression in PhoP$^c$ strains, i.e. repressed protein species of specific sizes.

Eight strains were identified with gene fusions to phoP-repressed genes. As shown in Table 6, the synthesis of most prg::TnphoA fusion proteins was fully repressed by the pho-24 allele. While two loci had complete repression of fusion protein activity, others demonstrated only partial repression. The expression of pags in PhoP$^c$ strains is 5–10 fold less than that observed after bacteria are phagocytosed by macrophages suggesting that the degree of repression of some prg loci may be greater when pags are maximally activated within acidified macrophage phagosomes.

Lower values for prgB -phoA fusions in strains with a wildtype phoP locus (Table 7B) compared to PhoP⁻ strains (Table 7) may represent some degree of repression in the presence of PhoP.

TABLE 6

| Allele | PhoP⁻ | PhoP$^c$ | Fold Repression |
| --- | --- | --- | --- |
| prgA1::TnphoA | 29 | 7 | 4 |
| prgB1::TnphoA | 137 | 27 | 5 |
| prgB2::TnphoA | 77 | 19 | 4 |
| prgC1::TnphoA | 14 | 1 | 14 |
| prgE1::TnphoA | 21 | 5 | 4 |
| prgE2::TnphoA | 34 | 6 | 6 |
| prgE3::TnphoA | 25 | 6 | 4 |
| prgH1::TnphoA | 92 | 2 | 46 |

In Table 6, a comparison of the effect of phoP locus mutations on Prg-PhoA fusion protein activity is made. PhoP⁻ indicates that the strain assayed contains the phoP12 allele (CS030) and PhoP$^c$ indicates the strain assayed contains the pho-24 allele (CS031). Values were calculated from stationary phase cultures. The numbers denote representative values of experiments performed on three separate occasions and represent activity in units of alkaline phosphatase as defined above.

TABLE 7A

| Strain | Allele | Starvation Media | Rich Media |
| --- | --- | --- | --- |
| IB010 | prgB1::TnphoA | 21 | 26 |
| IB040 | prgH1::TnphoA | 7 | 181 |
| CS119 | pagC1::TnphoA | 1263 | 102 |

TABLE 7B

| Strain | Allele | Aerobic | Microaerophilic | Anaerobic |
| --- | --- | --- | --- | --- |
| IB010 | prgB1::TnphoA | 33 | 777 | 1521 |
| IB040 | prgH1::TnphoA | 142 | 85 | 41 |
| CS119 | pagC1::TnphoA | 431 | 173 | 81 |

TABLE 7C

| Strain | Allele | pH 4.5 | pH 7.0 |
| --- | --- | --- | --- |
| IB010 | prgB1::TnphoA | 332 | 26 |
| IB040 | prgH1::TnphoA | 8 | 18 |
| CS119 | pagC1::TnphoA | 145 | 27 |

Table 7 demonstrates the effects of environmental conditions on the in vitro regulation of prg loci. Table 7A shows the effect of starvation on prg and pag expression. Starvation medium (N⁻C⁻P⁻) (17) contained 0.04% glucose, 10 mM NH$_4$Cl, and 1 mM NaH$_2$PO$_4$.H$_2$O. The fusion protein activity for starvation media was measured after 48 hours of growth (OD$_{600}$=0.5) while that in rich media (LB) was measured in late-logarithmic growth (OD$_{600}$=1.0).* All cultures were grown aerobically.

Table 7B shows the effect of oxygen tension on expression of phoP-activated and phoP-repressed genes. Expression in rich medium is compared under aerobic conditions at stationary phase (OD$_{600}$>1.4), microaerophilic (OD$_{600}$=0.8), and strict anaerobic conditions with 80% N$_2$, 10% O$_2$, and 10% CO$_2$ (OD$_{600}$=0.6) after 24 hours of growth.*

Table 7C shows the effect of pH on the expression of fusion protein activity of prg and pag loci. Expression was measured from cultures grown to logarithmic growth (OD$_{600}$=0.5) in LB media buffered to various pHs with sodium citrate. All the numbers represent activity in units of alkaline phosphatase as defined above.

Chromosomal location of prg::TnphoA loci prg::TnphoA linkage analysis was performed to a bank of strains with randomly spaced Tn10Δ16Δ17 insertions to determine chromosomal locations and whether prg::TnphoA alleles were unlinked loci. The prg::TnphoA insertions were in five distinct linkage groups. Three alleles, prgE1–3::TnphoA were identically linked to the Tn10Δ16Δ17 insertion of AK3091 (26%) and two other alleles, prgB1–2::TnphoA were similarly linked to the Tn10Δ16Δ17 insertion of AK3190 (94%), AK3249 (89%), and AK3186 (50%). Another allele, prgH1::TnphoA, was found to be 37% linked to the Tn10Δ16Δ17 insertion of strain AK3304. The other two prg alleles did not demonstrate linkage to the bank of strains tested. The chromosomal DNA of these two strains was analyzed by Southern hybridization analysis using a portion of TnphoA as a probe, and a rough physical map of the sites located adjacent to the TnphoA insertion was determined. These alleles, prgA and prgC, had different restriction endonuclease sites surrounding the TnphoA insertions. In addition, the repression of prgA and prgC fusion protein activity in strains with the pho-24 mutation was different; prgC was completely repressed, while prgA was only partially repressed indicating that these loci are different. Thus, five unlinked loci encoding envelope proteins repressed in the PhoP$^c$ phenotype were identified.

Though three prg loci were identified that were linked to transposon insertions, none of the Tn10Δ16Δ17 insertions had a known map location. The physical map location of two of these transposon insertions, AK3249 and AK3304, was analyzed using XbaI restriction endonuclease digestion and pulse field gel electrophoresis (PFGE). Since Tn10Δ16Δ17 contains a single XbaI site, these Tn10Δ16Δ17 insertions can be assigned to a specific XbaI fragment of known map location (Liu et al., 1992, J. Bacteriol. 174:16622). AK3249 was assigned to 28–32 min, while AK3304 was assigned to either end of the 58–70 minute fragment. Further P22 transduction to known markers in those regions was performed. The Tn10Δ16Δ17 insertion of strain AK3249 and prgB1::TnphoA were found not to be linked to the Tn10 insertion of strain TN3061 (6% linked to dcp), which has a transposon insertion at 28 min, or to the ompD::Tn5 insertion of strain SH7782 at 32 min. prgH1::TnphoA was found to be very weakly linked to the srl202::Tn10 insertion of strain TT520 (<0.1%) at 59 minutes. These data indicate that prgs are unlinked on the Salmonella chromosome, consistent with the function of PhoP/PhoQ as global regulators.

The chromosomal location of TnphoA insertions in phoP-repressed genes (prg::TnphoA) was determined by linkage analysis to a bank of strains with Tn10Δ16Δ17 insertions (Kukral et al., 1987, J. Bacteriol. 169:1787, herein incorporated by reference). Cells with TnphoA insertions were spread on LB agar plates containing 10 μg/ml tetracycline and 40 μg/ml XP. Then P22 lysates grown on strains with Tn10Δ16Δ17 insertions were spotted onto plates with a multiprong inoculator. After overnight inoculation, plates were reviewed for linkage by looking for mixed blue and white colonies. Linkage was confirmed and quantitated by carrying out individual transductional crosses between the Tn10Δ16Δ17 containing strains and the strain with the TnphoA insertion. After selection for the Tn10Δ16Δ17 encoded tetracycline resistance, strains were scored for loss of blue color and TnphoA encoded kanamycin resistance. Some TnphoA strains were found to be linked to Tn10Δ16Δ17 strains with no known map location. Two of these Tn10Δ16Δ17 insertions were physically mapped using PFGE following XbaI restriction endonuclease digestion. Based on physical mapping, linkage analysis to other transposon insertions by P22 bacteriophage transduction was determined as necessary.

Chromosomal DNA was prepared as described by Mekalanos, 1983, Cell 35:253, herein incorporated by reference, using Proteinase K instead of Pronase. Purification of plasmid DNA was performed by standard methods. Restriction endonuclease digestion was performed according to the recommendations of the manufacturer (New England Biolabs). DNA, size fractionated in agarose gels, was transferred to Genescreen Plus membranes (New England Nuclear/Dupont, Boston, Mass.) for blot hybridization by the method of Southern well known in the art. DNA probes were purified from agarose gels by the freeze-squeeze method (Tautz et al., 1983, Anal. Biochem. 132:14) and radiolabelled with [$^{32}$P]dCTP by the random primer method (Feinberg et al., 1983, Anal. Biochem. 132:6).

Cloning Pro::Tnpho A fusions

The gene encoding prgH has been cloned using methods described below. The plasmid, pIB01, containing the prgH gene has been deposited with the American Type Culture Collection on Jul. 9, 1993 (Rockville, Md.) and has received ATCC designation 75496. FIG. 5 shows the partial DNA sequence of prgH (SEQ ID NO: 3).

The prg genes identified by ThphoA insertion can be cloned using previously described methods (Beattie et al., 1990, J. Bacteriol. 172:6997, herein incorporated by reference). Chromosomal DNA of each strain containing a prg::TnphoA gene fusion is digested with a restriction enzyme such as BamH1 which cuts at a single site in TnphoA maintaining the fusion junction, phoA sequences and the neo gene. Similarly, a plasmid such as pUC19 is digested with the same enzyme. Digested chromosomal and plasmid DNA are ligated overnight at 15° C. and transformed into competent E. coli. Transformations are plated on LB agar containing ampicillin and kanamycin to select for the bla gene of pUC19 and the neo gene of TnphoA. The chromosomal DNA containing the prg::TnphoA gene fusion can then be sequenced using standard methodology described above, such as the SEQUENASE® (United States Biochemical) kit. Universal primer (United States Biochemical) corresponding to DNA sequences in the plasmid or TnphoA primer (5'-AATATCGCCCTGAGCA-3') (SEQ ID NO:4) corresponding to bases 71 to 86 of TnphoA can be used as primers.

To clone the wild type prg gene, a fragment of chromosomal DNA flanking TnphoA sequences can be used to screen a cosmid gene bank of wild type strain ATCC 10428 using methods described above for cloning wild type pagC.

Environmental regulation of prg loci

Since PhoP/PhoQ are environmentally responsive regulators, the effects of different growth conditions on prg::TnphoA expression were tested. The growth rate of strains with prg::TnphoA insertions was comparable to wild-type organisms under all conditions. The expression of all prg loci was maximal in late logarithmic growth phase when bacteria were grown in rich (LB) media. An example of this is the comparison of values of prgH::TnphoA expression in Table 7A (rich media and stationary growth) and Table 7C (pH 7.0, log phase). Since the expression of pag loci was maximal in starvation (which only reaches a maximal OD$_{600}$=0.5) and stationary growth phase, this was consistent with a reciprocal relationship between the expression of pags and prgs. Further analysis of prg loci expression under starvation conditions confirmed this reciprocal relationship (Table 7A). prgH expression was repressed (Table 7A) and other prgs were minimally affected under starvation conditions, in contrast to the induction of pag expression when bacteria were starved (Table 7A).

Because of its role in bacterial-mediated endocytosis (BME), the effect of oxygen tension in rich medium on pag and prg expression was also tested (Table 7B). Different but not reciprocal regulation of pag and prg loci was found on growth at different oxygen tensions. Though pagA and pagB loci were minimally affected by growth at different oxygen tensions, the pagC virulence locus was approximately 5 fold repressed when bacteria were grown anaerobically as compared to aerobic growth (Table 7B). Variability was also noted in the expression of prg loci in response to growth conditions in the absence of oxygen. One loci, prgH, was repressed three-fold in anaerobic growth, while another locus, prgB, was induced almost 50-fold when grown anaerobically (Table 7B). Other prg loci had minimal change in fusion protein expression as a result of different oxygen tensions in the growth media.

Low pH conditions also had a variable effect on prg expression (Table 7C). The expression of pagC fusion protein activity was induced under acid conditions as previously known. When bacteria were grown to mid-logarithmic growth, no significant induction of the relative repression of prgH expression was noted in media of low pH, while prgB expression was induced on exposure of bacteria to low pH (Table 7C). Hence, loci maximally expressed under diverse environmental conditions can all be repressed by the PhoP$^c$ phenotype.

Acid sensitivity was tested by the method of Foster et. al., 1990, J. Bacteriol. 172:771, herein incorporated by reference. Strains were grown aerobically in E media and 0.4% glucose at 37° C. to an OD$_{600}$ of 0.5. The pH of the bacterial culture was decreased to near 3.3 by the addition of 1M hydrochloric acid. An aliquot was taken immediately ($t_o$), the remainder of the culture was incubated further at 37° C. with subsequent aliquots removed at 40 min ($t_{40}$) and 80 min ($t_{80}$) time points. The pH of the cultures remained near 3.3. The aliquots were diluted 1:10 in cold PBS, washed and resuspended in normal saline prior to plating serial dilutions for colony forming units.

prgH is a virulence locus for *S. typhimurium*

Since the PhoP$^c$ phenotype resulted in virulence attenuation and repressed the synthesis of approximately 20 proteins, the virulence of strains with single mutations in prg loci was tested (Table 8). Strains with prg::TnphoA insertions were screened for virulence defects by intraperitoneal injection of approximately 150 organisms into BALB/c mice. Controls were also performed with wild-type bacteria. A significantly longer time course of clinical disease progression was observed with a prg mutant strain compared to wild type bacteria. Mice injected intraperitoneally with strains containing the prgH1::TnphoA insertion developed clinical signs of typhoid fever, such as a "scruffy" phenotype (fever and piloerection) and hepatosplenomegaly in approximately 10–14 days, compared to approximately 24 hours for the wild type bacteria. Despite the extended time course of disease development, all the mice eventually died. Disease progression of mice injected with other strains containing prg::TnphoA insertions showed a similar pattern of illness to that of wild type bacteria.

TABLE 8

| | | LD$_{50}$ |
|---|---|---|
| Intraperitoneal infection | | |
| 14028s | Wild type | <10 |
| IB040 | prgH1 | 5.6 × 10$^1$ (16) |
| CS015 | phoP-102 | 6.7 × 10$^5$ (29) |
| IB041 | prgH phoP-102 | 1.2 × 10$^7$ (31) |
| Oral inoculation | | |
| 14028s | Wild type | 6.5 × 10$^4$ (35) |
| IB040 | prgH1 | 6.5 × 10$^5$ (21) |

Table 8 shows the effect of the prgH1::TnphoA mutation on Salmonella mouse virulence. Strains were isogenic and administered by intraperitoneal injection and oral inoculation in 35 day old BALB/c mice. The number of animals used at bacterial dilutions near the LD$_{50}$ for each allele is listed in parentheses. The LD$_{50}$ determinations were repeated on three separate occasions.

Further testing of the LD$_{50}$ of strains containing prgH mutations was performed. prgH mutants were determined to have an LD$_{50}$ of approximately 60 organisms compared to a value of <10 for wild type bacteria. Due to the difficulty in accurately delivering organisms in small doses to mice, a strain with a mutation in both prgH and phoP was constructed. The PrgH$^-$PhoP$^-$ strain had greater than a 10 fold increase in LD$_{50}$ compared to CS015, an isogenic PhoP$^-$ strain (Table 8). The combined effect of the two mutations further documented that the prgH1::TnphoA mutation attenuated *S. typhimurium* virulence and indicated that mutations which affected two phases of PhoP/PhoQ regulated gene expression were additive in their effect on virulence. Strains with prgH1::TnphoA insertions were also tested for virulence when administered by the oral route. A 10 fold decrease in virulence (increase in LD$_{50}$) was observed (Table 8).

Further analysis of the efficiency of strains with prgH1::TnphoA insertions in crossing the mucosal barrier was tested by competition experiments with wild-type bacteria. During the first 72 hours after oral inoculation with mutant bacteria, no prgH1::TnphoA mutants were recovered from the bloodstream of mice compared to control experiments in which organisms were routinely isolated from the blood of mice inoculated with wild type bacteria. Other strains with prg mutations were also tested for virulence defects by the oral route, but no significant change in virulence was observed.

Mouse virulence studies were carried out as follows. Bacteria were grown aerobically at 37° C. to stationary phase, washed with LB, and diluted in normal saline. 35 days old (16–18 g) female BALB/c mice were purchased from the Charles River Breeding Laboratories, Inc. (Wilmington, Mass.). Diluted bacterial samples in saline were injected intraperitoneally with an inoculum of 0.1–0.15 ml. Bacteria were administered orally as a 0.5 ml bolus to mice fasted for 2 hours, via a 2 inch straight, 18 gauge stainless steel animal oral feeding needle (Harvard Apparatus, Inc., South Natick, Mass.) under mild 2-bromo-2-chloro-1,1,1-trifluoroethane (Halothane) anesthesia. The number of organisms administered was quantitated by plating for cfu/ml on LB agar. Mouse 50% lethal dose (LD$_{50}$) values were determined by standard methods (Reed and Muench, 1938, Amer. J. Hygiene 27:493). The LD$_{50}$ determinations were repeated on three separate occasions. Competition assays were performed after bacteria were administered orally to mice as above. Bacteremia was assessed on days 1–4 from tail bleeds or intracardiac punctures with 50 μl of blood plated immediately and after growth in LB broth at 37° C. overnight. Spleen and intestinal harvests were performed on days 1–6 with organs homogenized in 3 mls of 0.9% sodium chloride. Samples and cultures were plated in serial dilutions. *S. typhimurium* was confirmed by characteristic growth (black colonies) on Hektoen-enteric agar (Difco Laboratories) and by the macroscopic slide agglutination test with Salmonella rabbit serum Group B (Antigens 4, 5, 12) (Fisher Scientific).

Mutations in oxygen-induced genes do not affect mouse virulence

Both prgH and pagC loci were shown to be repressed by anaerobic growth and required for full virulence, thus suggesting that a shift from anaerobic to aerobic conditions might serve as a general signal for induction of virulence genes. Strains with mutations in oxygen-inducible loci (Aliabadi et al., 1986, J. Bacteriol. 165:780) were constructed. ATCC14028s derivatives with oxiA, oxiC, and oxiE mutations were made (termed CS032, CS033, CS034, respectively). These strains were as virulent as wild type bacteria. Though these gene fusions could still mark operons containing virulence genes, this data suggests that these loci are not essential to full virulence and that oxygen induction is not always correlated with virulence function.

PrgH mutants have normal survival within macrophages

Since the PhoP$^c$ phenotype resulted in a defect in bacterial survival within macrophages, the effect of this mutation on the synthesis of a prgH-encoded protein was tested. A strain with the prgH1::TnphoA insertion was tested for intracellular survival within bone marrow-derived macrophages from BALB/c mice and J774.2 cells, a macrophage derived cell line. No defect in intracellular survival was observed. A strain with a prgB1::TnphoA insertion was also tested and found not to have a defect in survival within macrophages.

Assays to determine bacterial survival within macrophages were performed as described by Buchmeier al., 1989, Infect. Immun. 57:1, herein incorporated by reference. Bacteria grown to stationary-phase were opsonized for 30 minutes in normal mouse serum before exposure to cultured bone marrow-derived macrophages harvested from BALB/c mice. One hour after infection, gentamicin 10 μg/ml was added to kill extracellular bacteria. All time points (1, 4, and 24 hr) were done in triplicate and repeated on three separate occasions.

Cultured bone marrow macrophages were harvested from BALB/c mice purchased from the Charles River Breeding Laboratories. J774.2 macrophages were cultured in Dulbecco's minimal essential medium with 10% fetal bovine serum (DMEM/10% FBS).

prg::TnphoA insertions do not suppress the phenotyoes of PhoP mutants

Several phenotypes of phoP mutants, including defensin and acid sensitivity as well as mouse virulence attenuation, were tested for suppression on addition of a prg::TnphoA mutation. To test the ability of a phoP mutation to suppress the synthesis of prg products, PhoP mutant strains isogenic except for prg::TnphoA mutations were constructed and tested for mouse virulence, where suppression would involve an increase in virulence, or decreased acid and defensin sensitivity. prg::TnphoA insertions had no effect on the virulence phenotypes of PhoP⁻ bacteria. These results indicate that the prg::TnphoA mutations tested did not suppress the PhoP null phenotype as single mutations.

PrgH and PhoP$^c$ mutants are defective in bacterial-mediated endocytosis by cultured epithelial cells The BME of prg::TnphoA and PhoP$^c$ S. typhimurium strains was tested. The following observations (described herein) suggested that prg genes may be involved in bacterial-mediated uptake by eucaryotic cells: prgH1::TnphoA was shown to be located at 59' on the bacterial chromosome, a location where other genes essential to invasion are clustered; prgH mutants were shown to be defective in competition with wild type organisms on reaching the bloodstream of mice in the first 72 hours after oral ingestion; and the expression of one prg locus, prgB, was dramatically induced under anaerobic growth conditions. Strains with prgH and pho-24 mutations had a significant reduction (p-value<0.01) in their ability to induce uptake by Madin-Darby canine kidney (MDCK) polarized epithelial cells compared to wild-type bacteria. Other prg strains with TnphoA insertions did not demonstrate a statistically significant defect in BME by epithelial cells (Table 9). The adherence of strains defective in BME was unaffected by the prgH::TnphoA insertion when determined by cell-associated cfu/ml before the administration of gentamicin (Table 9) and by microscopy.

To assay bacterial adherence and uptake of bacteria by epithelial cells, bacterial strains were grown at 37° C. without shaking (microaerophilic) to a final density of approximately 2×10⁸ colony forming units (cfu)/ml. Assays were performed by seeding 10⁵ MDCK cells/well in 24-multiwell tissue culture plates. Cells were incubated overnight at 37° C. in 5% CO₂/95% air atmosphere in DMEM/10% FBS without antibiotics until >80% confluent.

The adherence and invasion assays were carried out according to the protocol of Lee and Falkow, 1990, Proc. Natl. Acad. Sci. U.S.A. 87:4304, herein incorporated by reference.

TABLE 9

| Strain | Genotype | Adherence | Invasion |
|---|---|---|---|
| 14028s | Wild type | 4.2% | 3.8% |
| SM7 | Str$^r$ smb | — | 0.6%* |
| CS119 | pagC1::TnphoA | — | 1.9% |
| IB005 | prgA1::TnphoA | — | 7.6% |
| IB010 | prgB1::TnphoA | — | 2.9% |
| IB020 | prgC1::TnphoA | — | 1.5% |
| IB025 | prgE1::TnphoA | — | 1.9% |
| IB040 | prgH1::TnphoA | 5.7% | 0.1%* |
| CS022 | pho-24 | 1.9% | 0.06%* |
| IB043 | pWKSH5 in IB040 | — | 17.5%* |
| IB044 | pWKSH5 in CS022 | — | 0.09%* |

In table 9, the effect of prg::TnphoA insertions on Salmonella-mediated endocytosis by MDCK epithelial cells is shown. Microaerophilically grown bacterial strains were assessed for changes in adherence and invasion. Adherence was determined as the percentage of bacteria adhered to the cells after centrifugation and 30 minute 4° C. incubation/total number of bacteria added to each well. Invasion was determined as the percentage of bacteria that had invaded after a two hour incubation with gentamicin/total number of bacteria added to each well. There was no difference between S. typhimurium wildtype and S. enteritidis CDC5 wildtype strains with respect to adherence and invasion frequency. The asterisk * represents statistical significance by variance analysis of the invasion data done in triplicate compared to wild-type (p-value<0.01).

The confluent MDCK monolayers were washed three times with PBS, then 0.9 ml of cold DMEM/10% FBS was added to each well. Bacteria were washed in LB and resuspended in an equivalent volume of DMEM/10% FBS. Approximately 5×10⁷ bacteria were added/well. The plates were spun at 500 rpm at 4° C. for 10 minutes, then incubated at 4° C. for 30 minutes. Adherent bacteria were recovered by washing the plates three times with phosphate-buffered saline (PBS), lysing the epithelial cells in 0.5 ml of 1% Triton-X-100/PBS, and plating for cfu/ml on LB agar. A morphologic assessment of adherence was also performed by staining bacterially infected epithelial cell monolayers grown overnight on coverslips for 7 minutes in 1 μg/ml 4' 6-diamidino-2-phenylindole (DAPI). These DAPI stained coverslips were examined by both fluorescent and phase contrast microscopy using a Leitz Laborlux 12 microscope.

Invasion or bacterial-mediated endocytosis (BME) was assessed by allowing bacteria to adhere as described above. Plates containing bacteria and epithelial cells were incubated for two hours at 37° C. in a 5% CO₂/95% air atmosphere. Each well was washed three times with PBS to remove bacteria not associated with cells. DMEM/10% FBS supplemented with 10 μg/ml gentamicin was then added to kill extracellular bacteria. After 90 minutes of incubation, the cell monolayers were washed three times with PBS and the viable intracellular bacteria were released by vigorously pipetting with 0.5 ml of 1% Triton X-100/PBS. An invasion deficient Salmonella enteritidis mutant and an invasive clinical wild-type isolate of S. enteritidis were used as controls for BME. Viable bacteria were quantitated by plating for cfu/ml on LB agar medium. All assays were done in triplicate and repeated at least three times.

MDCK epithelial cells were used between passage 40–58 to maximize bacterial adherence and invasion. Epithelial cell lines were cultured in DMEM/10% FBS and 1% penicillin/streptomycin solution at 37° C. in a 5% $CO_2$ atmosphere.

To assay bacterial defensin sensitivity, NP-1 defensin was purified from rabbit peritoneal neutrophils according to methods known in the art (Selsted et al., 1985, J. Biol. Chem. 260:4579; Selsted et al., 1984, Infect. Immun. 45:655). Typically, $10^5$ bacteria in 0.5% tryptone in 100 μl volume were exposed to 50–100 μg of defensin/ml at 37° C. for 2 hours. The reactions were stopped by diluting the reaction in 0.9% NaCl. Appropriate dilutions were plated to determine the cfu/ml of surviving bacteria. Assays were performed in duplicate at least twice for each strain. Appropriate assays with sensitive (PhoP−) and resistant (wild-type) strains were performed as controls.

Mapping of prgH

The location of prgH relative to other invasion loci at 59 minutes was determined using linkage analysis. P22 transduction linkage analysis indicated that the Tn10Δ16Δ17 of strain AK3304 had similar linkage to invA (40%) and prgH (37%); however, invA was not linked to sorbital. The prgH1::TnphoA insertion was found to be linked (99.6%) to the transposon insertion of EE517, a strain with a 8.5 kilobase deletion adjacent to the Tn5B50-378 insertion of hil.

A physical map of the restriction endonuclease sites surrounding the TnphoA insertion of strain IB037 was made (FIG. 4) revealing no similarities to the known restriction endonuclease map of the invA-E region. Plasmids containing the cloned inv and hil DNA were then used as probes in Southern hybridization analysis of chromosomal DNA from wild type ATCC10428s and IB040 bacteria containing the prgH1::TnphoA insertion. When a plasmid which contains other invasion loci highly linked to invA-E (invH, invF, and part of invG) was used as a probe, no differences in hybridization pattern was found between wild type bacteria and strain IB040 indicating that prgH was not located within the inv region. However, when a plasmid containing a 5 kb region immediately downstream of the Tn5B50-380 insertion of hil was used as a probe, the prgH1::TnphoA insertion was demonstrated to be located within this region. By use of the known restriction map of the hil locus (Lee et al., 1992, Proc. Natl. Acad. Sci. U.S.A. 89:1847) and the known restriction endonuclease sites of TnphoA, the physical map of this area and the relationship of prgH1::TnphoA within it were further defined (FIG. 4). The prgH1::TnphoA insertion was oriented so that the direction of transcription of the phoA fusion protein was opposite to that of the Tn5B50 insertions that confer the hil phenotype and contain a constitutive neomycin promoter that is transcribed out of the transposon (FIG. 4). Althought prgH was found to be located within the hil locus, this gene is unique in that it is oppositely transcribed and unlike any other genes identified within the hil locus, prgH is regulated by the phoP regulon.

Since it was possible that a protein whose expression was altered by the Tn5B50-380 insertion might alter the expression of prgH, strains containing both insertions were constructed and the prgH-phoA fusion protein activity compared under different environmental conditions. When bacteria were starved or grown anaerobically, derepression of fusion protein activity was observed. Table 11 shows the effect of the Tn5B50-380 insertion on expression of prgH fusion protein activity.

TABLE 11

| Strain | Allele | Starvation | LB (aerobic) | LB (anaerobic) |
|---|---|---|---|---|
| IB040 | prgH1::TnphoA | 5 | 142 | 41 |
| IB042 | Tn5B50-380 prgH1::TnphoA | 46 | 248 | 227 |

This data demonstrates that the Tn5B50-380 insertion increased prgH expression, even though prgH transcription was opposite to that of the Tn5B50-380 encoded neomycin promoter. Starvation (repressing conditions for prgs) indicates that bacteria were grown aerobically for 48 hours in starvation medium ($N^-C^-P^-$) (17) containing 0.04% glucose, 10 mM $NH_4Cl$, and 1 mM $NaH_2PO_4.H_2O$. LB (aerobic) indicates that bacteria were grown in Luria-Bertani broth (rich media) to late logarithmic growth (nonrepressing conditions) ($OD_{600}$ >1.0). LB (anaerobic) indicates that bacteria were grown under strict anaerobic conditions for 24 hours ($OD_{600}$=0.6). All the numbers represent activity in units of alkaline phosphatase as described above.

To rule out the possibility that the BME defect of the prgH mutant was an artifact of the PhoA fusion protein produced, complementation analysis was performed with a plasmid (pWKSH5) containing a 5.1 kb HindIII fragment which included the hil and prgH loci. The plasmid was crossed into PrgH (IB040) and PhoP$^c$ (CS022) mutant bacteria to create strains IB043 and IB044, respectively. The BME phenotype of the PrgH mutant was similar to wild-type with the same plasmid insertion. The BME phenotype of the PhoP$^c$ mutant was not complemented by this plasmid. These results indicate that a gene product altered in synthesis as a result of the prgH::TnphoA insertion was necessary for BME.

Using a strain with a phoP/phoQ locus mutation that constitutively simulates the environmental activation of pags (phenotype PhoP$^c$), five unique phoP-repressed loci encoding envelope proteins were defined. phoP-repressed genes (prgs) were found to be widely spaced on the chromosome and the expression of prg loci was repressed under starvation conditions, when pag loci were induced (Table 10).

TABLE 10

| Environment | pags | prgs |
|---|---|---|
| media | starvation | rich |
| $O_2$ | aerobic - pagC | aerobic - prgH |
|  |  | anaerobic - prgB |
| pH | 3.3–5.5 | 3.3–5.5 - prgB |
|  |  | >6.0 - prgH |
| mammalian cell | macrophage | epithelial |

PrgH was shown to lie between two Tn5B50 insertions that confer the hil phenotype. Since deletion mutants in this region have been demonstrated to also have defects of BME, and the BME defect of prgH mutants can be complemented with a plasmid containing this locus, it is possible that a protein not synthesized as a result of the prgH1::TnphoA insertion promotes BME (FIG. 4).

Contrary to the expectation that genes essential to the hil phenotype would be induced under microaerophilic conditions similar to what was found for prgB, prgH expression was maximal during aerobic growth and the Tn5B50-380 insertion, which results in a hil phenotype, derepressed expression of prgH. In addition, the direction of transcription predicted by the prgH1::TnphoA insertion is opposite to that of the Tn5B50-380 encoded neomycin promoter associated with the hil phenotype suggesting that a regulatory protein interrupted by or transcribed from the Tn5B50-380 insertion affects the expression of prgH.

In view of the observation that pWKSH5, a plasmid containing prgH (hil), did not complement PhoP$^c$ bacteria for BME, it is possible that other invasion genes may also be regulated by PhoP/PhoQ. If prgH was expressed from pWKSH5, despite the presence of the pho-24 mutation, this suggests that other genes repressed as part of the PhoP$^c$ phenotype are necessary for BME.

The identification and characterization of prgH has shown that PhoP/PhoQ oppositely regulate factors necessary for bacteria to enter or to survive within mammalian cells, further documenting the importance of gene regulation to bacterial virulence. The identification of prg loci can be used to study the regulation of bacterial genes after infection of mammalian cells. Understanding the regulation of virulence genes, such as prgH can also be used to attenuated pathogenic bacteria for the development of new live vaccines for typhoid fever.

Role of prg genes in virulence

The prg locus, prgH, was found to contribute to mouse virulence when *S. typhimurium* was administered by both the oral and intraperitoneal routes. PrgH as well as PhoP$^c$ mutants were further found to be defective in bacterial-mediated uptake by epithelial cells suggesting that an inability to cross epithelial barriers might contribute to the attenuation of virulence observed. Competition studies in mice after oral ingestion of bacteria further supported that prgH mutants were defective in transcytosis across the intestinal epithelial barrier. Therefore, at least two phases of PhoP/PhoQ regulated protein expression essential to bacterial virulence have been defined. In one phase, prg expression promotes bacterial mediated endocytosis by epithelial cells (Table 10), while in another phase, pag expression promotes survival within macrophages.

Systemic pathogens, such as Salmonella, may encounter more complex and varied environments than may be encountered by mucosal pathogens. The achievement of intermediate states of pag and prg expression could be essential to virulence at some stage of the infectious cycle. Consistent with this concept was the lack of uniformity observed in the expression of pags and prgs on growth at different oxygen tensions and pH conditions. These data may also indicate that not all regulation of pags and prgs is mediated directly through PhoP and PhoQ. Given the function of PhoP as a transcriptional regulator, it is likely that prg loci repression occurs at the level of transcription.

The approach of defining genes repressed by the pho-24 mutation has led to the discovery of at least one virulence locus, prgH, which can be mutated to attenuate the bacteria for vaccine purposes.

Attenuation of Bacterial Virulence by Constitutive Expression of Two-component Regulatory Systems.

The virulence of a bacterium can be attenuated by inducing a mutation which results in the constitutive expression of genes under the control of a two-component regulatory system or by inducing a mutation that inactivates a gene under the control of the two-component systems. A balance between the expression of the genes under the control of the two-component system, e.g., between pag and prg gene expression, and possibly between two-component system regulated genes and other genes, is necessary for full virulence. Mutations that disrupt this balance, e.g., mutations that cause the constitutive expression of a gene under the control of the two-component system, or a mutation that inactivates a gene under the control of the two-component system, e.g., the pag gene, reduce virulence.

Constitutive mutations in two-component regulators can be identified by the use of a strain containing a recorder gene fusion to a gene regulated by the two-component system. Such gene fusions would most typically include DNA encoding the lacZ gene or alkaline phosphatase fused to a gene under the control of the two-component system. Strains containing fusions that are (as compared to wild type or parental strains) highly expressed in an unregulated fashion, i.e., constitutive, can be detected by increased color on chromogenic substrates for the enzymes. To detect constitutive mutations a cloned virulence regulator could be mutagenized e.g., by passage through an *E. coli* strain defective in DNA repair or by chemical mutagenesis. The mutated DNA for the regulator would then be transferred to the strain containing the gene fusion and constitutive mutations identified by the high gene fusion expression (blue color in the case of a lacZ fusion grown on media containing X-gal). Constitutive mutations in a component of a two-component regulatory system could also be made by in vitro mutagenesis after other constitutive mutations have been sequenced and a specific amino acid change responsible for the constitutive phenotype identified. Putting several amino acid changes that all result in a PhoP constitutive phenotype would result in a decreased frequency of reversion by spontaneous base changes. A constitutive mutation could also be constructed by deletion of the portion of the amino terminus of the phospho-accepting regulator which contains the phosphoacceptor domain e.g., deletion of sequences encoding amino acids amino terminal to amino acid 119 in the phoP gene or deletion of analogous phospho accepting sequences in genes of other two-component regulatory systems. This could result in a conformational change similar to that induced by phosphorylation and result in increased DNA binding and transcriptional activation.

Use

The Salmonella cells of the invention are useful as sources of immunological protection against diseases, e.g., typhoid fever and related diseases, in an animal, e.g., a mammal, e.g., a human, in particular as the basis of a live-cell vaccine capable of colonizing the inoculated animal's intestine and provoking a strong immune reaction. Appropriate dosages and conditions of administration of such a live, attenuated vaccine are as described in Holem et al., *Acute Enteric Infections in Children, New Prospects for Treatment and Prevention* (1981) Elsevier/North-Holland biomedical Press, Ch. 26, pp. 443 et seq. (Levine et al.), hereby incorporated by reference.

Other Embodiments

Other embodiments, e.g., strains which in addition to a phoP related mutation or genetic alteration also contain an attenuating mutation in another gene, e.g., an aromatic amino acid synthetic gene, e.g., aroA or aroD, or in cya gene (adenylate cyclase) or crp gene (adenylate cyclase receptor) are also within the claims.

What is claimed is:

1. A vector comprising a first DNA sequence encoding a heterologous protein, a second DNA sequence encoding a marker, and a third DNA sequence encoding a mutationally inactivated gene product of a phoP regulatory region-regulated Salmonella virulence gene, wherein said third sequence mediates integration of said first sequence into a Salmonella chromosome.

2. The vector of claim 1, wherein said phoP regulatory region regulated gene is a prg locus.

3. The vector of claim 1, wherein said phoP regulatory region regulated gene is a pag locus.

4. The vector of claim 1, wherein said first DNA sequence is within said third DNA sequence.

5. The vector of claim 1, wherein said vector cannot replicate in a wild-type Salmonella strain.

6. The vector of claim 1, wherein said first DNA sequence encoding a heterologous protein is under the control of an environmentally regulated promoter.

7. The vector of claim 1, further comprising a DNA sequence encoding T7 polymerase under the control of an environmentally regulated promoter and a T7 transcriptionally sensitive promoter, said T7 transcriptionally sensitive promoter controlling the expression of said first DNA sequence encoding a heterologous protein.

8. The vector of claim 2, wherein said gene is prgH.

9. The vector of claim 2, wherein said gene is prgA, prgB, prgC, or prgE.

10. The vector of claim 3, wherein said pag locus is pagC.

11. The vector of claim 6, wherein said promoter directs macrophage-specific expression of said heterologous protein.

12. The vector of claim 11, wherein said promoter is a Salmonella pagC promoter.

13. A vector comprising DNA which encodes the pagC gene product.

14. A vector comprising DNA which encodes the prgH gene product.

15. A vector comprising a first DNA sequence comprising a Salmonella pagC promoter and a second DNA sequence encoding a heterologous protein, wherein said pagC promoter directs macrophage-specific expression of said heterologous protein.

16. A vector comprising
a first DNA sequence encoding a heterologous protein, and
a second DNA sequence encoding a mutationally inactivated gene product of a phoP regulatory region-regulated Salmonella virulence gene, wherein said second sequence mediates integration of said first sequence into a Salmonella chromosome.

17. The vector of claim 16, wherein said phoP regulatory region regulated gene is a prg locus.

18. The vector of claim 16, wherein said phoP regulatory region regulated gene is a pag locus.

19. The vector of claim 16, wherein said first DNA sequence is within said second DNA sequence.

20. The vector of claim 16, wherein said vector cannot replicate in a wild-type Salmonella strain.

21. The vector of claim 16, wherein said first DNA sequence encoding a heterologous protein is under the control of an environmentally regulated promoter.

22. The vector of claim 16, further comprising a DNA sequence encoding T7 polymerase under the control of an environmentally regulated promoter and a T7 transcriptionally sensitive promoter, said T7 transcriptionally sensitive promoter controlling the expression of said first DNA sequence encoding a heterologous protein.

23. The vector of claim 17, wherein said gene is prgH.

24. The vector of claim 17, wherein said gene is prgA, prgB, prgC, or prgE.

25. The vector of claim 18, wherein said pag locus is pagC.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 2320
      (B) TYPE: nucleic acid
      (C) STRANDEDNESS: single
      (D) TOPOLOGY: linear (xi) SEQUENCE DESCRIPTION: SEQ ID NO: 1:

```
GTTAACCACT CTTAATAATA ATGGGTTTTA TAGCGAAATA CACTTTTTTA TCGCGTGTTC      60

AATATTTGCG TTAGTTATTA TTTTTTTGGA ATGTAAATTC TCTCTAAACA CAGGTGATAT     120

TTATGTTGGA ATTGTGGTGT TGATTCTATT CTTATAATAT AACAAGAAAT GTTGTAACTG     180

ATAGATATAT TAAAAGATTA AATCGGAGGG GGAATAAAGC GTGCTAAGCA TCATCGTGAA     240

TATGATTACA GCGCCTGCGA TGGCATATAA CCGTATTGCG GATGGAGCGT CACGTGAGGA     300

CTGTGAAGCA CAATGCGATA TGTTCTGATT ATATGGCGAG TTTGCTTAAT GACATGTTTT     360

TAGCCGAACG GTGTCAAGTT TCTTAATGTG TTGTGAGAT TTTCTCTTTA AATATCAAAA      420

TGTTGCATGG GTGATTTGTT GTTCTATAGT GGCTAAAGAC TTTATGGTTT CTGTTAAATA     480

TATATGCGTG AGAAAAATTA GCATTCAAAT CTATAAAAGT TAGATGACAT TGTAGAACCG     540

GTTACCTAAA TGAGCGATAG AGTGCTTCGG TAGTAAAAAT ATCTTTCAGG AAGTAAACAC     600

ATCAGGAGCG ATAGCGGTGA ATTATTCGTG GTTTTGTCGA TTCGGCATAG TGGCGATAAC     660

TGAATGCCGG ATCGGTACTG CAGGTGTTTA AACACACCGT AAATAATAAG TAGTATTAAG     720

GAGTTGTT                                                              728
```

```
ATG AAA AAT ATT ATT TTA TCC ACT TTA GTT ATT ACT ACA AGC GTT TTG       776
Met Lys Asn Ile Ile Leu Ser Thr Leu Val Ile Thr Thr Ser Val Leu
              5                  10                  15

GTT GTA AAT GTT GCA CAG GCC GAT ACT AAC GCC TTT TCC GTG GGG TAT       824
Val Val Asn Val Ala Gln Ala Asp Thr Asn Ala Phe Ser Val Gly Tyr
             20                  25                  30

GCA CGG TAT GCA CAA AGT AAA GTT CAG GAT TTC AAA AAT ATC CGA GGG       872
Ala Arg Tyr Ala Gln Ser Lys Val Gln Asp Phe Lys Asn Ile Arg Gly
         35                  40                  45

GTA AAT GTG AAA TAC CGT TAT GAG GAT GAC TCT CCG GTA AGT TTT ATT       920
Val Asn Val Lys Tyr Arg Tyr Glu Asp Asp Ser Pro Val Ser Phe Ile
     50                  55                  60

TCC TCG CTA AGT TAC TTA TAT GGA GAC AGA CAG GCT TCC GGG TCT GTT       968
Ser Ser Leu Ser Tyr Leu Tyr Gly Asp Arg Gln Ala Ser Gly Ser Val
65                  70                  75                  80

GAG CCT GAA GGT ATT CAT TAC CAT GAC AAG TTT GAG GTG AAG TAC GGT      1016
Glu Pro Glu Gly Ile His Tyr His Asp Lys Phe Glu Val Lys Try Gly
                 85                  90                  95

TCT TTA ATG GTT GGG CCA GCC TAT CGA TTG TCT GAC AAT TTT TCG TTA      1064
Ser Leu Met Val Gly Pro Ala Tyr Arg Leu Ser Asp Asn Phe Ser Leu
            100                 105                 110

TAC GCG CTG GCG GGT GTC GGC ACG GTA AAG GCG ACA TTT AAA GAA CAT      1112
Tyr Ala Leu Ala Gly Val Gly Thr Val Lys Ala Thr Phe Lys Glu His
        115                 120                 125

TCC ACT CAG GAT GGC GAT TCT TTT TCT AAC AAA ATT TCC TCA AGG AAA      1160
Ser Thr Gln Asp Gly Asp Ser Phe Ser Asn Lys Ile Ser Ser Arg Lys
    130                 135                 140
```

```
ACG GGA TTT GCC TGG GGC GCG GGT GTA CAG ATG AAT CCG CTG GAG AAT    1208
Thr Gly Phe Ala Trp Gly Ala Gly Val Gln Met Asn Pro Leu Glu Asn
145                 150                 155                 160

ATC GTC GTC GAT GTT GGG TAT GAA GGA AGC AAC ATC TCC TCT ACA AAA    1256
Ile Val Val Asp Val Gly Tyr Glu Gly Ser Asn Ile Ser Ser Thr Lys
                165                 170                 175

ATA AAC GGC TTC AAC GTC GGG GTT GGA TAC CGT TTC TGA AAAGC          1300
Ile Asn Gly Phe Asn Val Gly Val Gly Tyr Arg Phe
            180                 185

ATAAGCTATG CGGAAGGTTC GCCTTCCGCA CCGCCAGTCA ATAAAACAGG GCTTCTTTAC   1360

CAGTGACACG TACCTGCCTG TCTTTTCTCT CTTCGTCATA CTCTCTTCGT CATAGTGACG   1420

CTGTACATAA CATCTCACTA GCATAAGCAC AGATAAAGGA TTGTGGTAAG CAATCAAGGT   1480

TGCTCAGGTA GGTGATAAGC AGGAAGGAAA ATCTGGTGTA ATAACGCCA GATCTCACAA    1540

GATTCACTCT GAAAAATTTT CCTGGAATTA ATCACAATGT CATCAAGATT TTGTGACCGC   1600

CTTCGCATAT TGTACCTGCC GCTGAACGAC TACTGAAAAG TAGCAAGGTA TGTATTTTAT   1660

CCAGGAGAGC ACCTTTTTTG CGCCTGGCAG AAGTCCCCAG CCGCCACTAG CTCAGCTGGA   1720

TAGAGCATCA ACCTCCTAAG TTGATGGTGC GAGGTTCGAG GCCTCGGTGG CGGTCCAATG   1780

TGGTTATCGT ATAATGTTAT TACCTCAGTG TCAGGCTGAT GATGTGGGTT CGACTCCCAC   1840

TGACCACTTC AGTTTTGAAT AAGTATTGTC TCGCAACCCT GTTACAGAAT AATTTCATTT   1900

ATTACGTGAC AAGATAGTCA TTTATAAAAA ATGCACAAAA ATGTTATTGT CTTTTATTAC   1960

TTGTGAGTTG TAGATTTTTC TTATGCGGTG AATCCCCCTT TGCGGCGGGG CGTCCAGTCA   2020

AATAGTTAAT GTTCCTCGCG AACCATATTG ACTGTGGTAT GGTTCACCGG GAGGCACCCG   2080

GCACCGCAAT TTTTTATAAA ATGAAATTCA CACCCTATGG TTCAGAGCGG TGTCTTTTTA   2140

CATCAGGTGG GCAAGCATAA TGCAGGTTAA CTTGAAAGAT ACGATCAATA GCAGAAACCA   2200

GTGATTTCGT TTATGGCCTG GGGATTTAAC CGCGCCAGAG CGTATGCAAG ACCCTGGCGC   2260

GGTTGGCCGG TGATCGTTCA ATAGTGCGAA TATGAATGGT TACCAGCCGC CTGCGAATTC   2320

(2) INFORMATION FOR SEQ ID NO:    2:

(i) SEQUENCE CHARACTERISTICS:
        (A) LENGTH: 53
        (B) TYPE:   nucleic acid
        (C) STRANDEDNESS: single
        (D) TOPOLOGY:    linear (xi) SEQUENCE DESCRIPTION: SEQ ID NO: 2:

CATTTCTCAT TGATAATGAG AATCATTATT GACATAATTG TTATTATTTT ACG           53

(2) INFORMATION FOR SEQ ID NO:    3:

(i) SEQUENCE CHARACTERISTICS:
        (A) LENGTH: 688
        (B) TYPE:   nucleic acid
        (C) STRANDEDNESS: single
        (D) TOPOLOGY:    linear (xi) SEQUENCE DESCRIPTION: SEQ ID NO: 3:

GAGCGCATTA TCAGATAAAT TGATTTATTT CTCACTTTCA TTCTATTTTC ATCAGGAATC    60

CCTGTGTCCT GTGCGGTAAT CTGCTGCTAT CGAGAACGAC AGACATCGCT AACAGTATAT   120

ATGGAAACAT CAAAAGAGAA GACGATAACA AGCCCAGGGC CATACATAGT TCGATTACTT   180

AACAGCTCAC TGAACGGCTG TGAGTTTCCA TTGCTGACAG GCCGAACACT CTTTGTGGTA   240

GGTCAGAGTG ATGCGCTCAC TGCTTCAGGT CAACTCCCTG ATATACCTGC CGATAGCTTT   300
```

-continued

```
TTTATCCCGC TGGACCATGG CGGAGTAAAT TTTGAAATCC AGGTGGATAC GGATGCGACC      360

GAAATTATAC TCCATGAGCT GAAAGAAGGA AATTCTGAAT CTCGTTCGGT GCAATTAAAT      420

ACGCCAATAC AGGTCGGTGA ATTGCTTATC CTGATTCGCC CGGAAAGCGA GCCGTGGGTG      480

CCCGAGCAGC CTGAGAAGTT AGAAACGTCT GCAAAAAAGA ACGAGCCGCG TTTTAAAAAC      540

GGAATTGTAG CAGCACTGGC CGGGTTTTTT ATATTGGGAA TTGGGACTGT GGGGACGTTA      600

TGGATACTTA ACTCGCCGCA GCGGCAGGCC CGAGAGCTCG ATTCGTTATT GGGGCAGGAG      660

AAGGAGCGTT TTCAGGTGTT GCCAGGCC                                        688
```

(2) INFORMATION FOR SEQ ID NO: 4:

(i) SEQUENCE CHARACTERISTICS:
        (A) LENGTH: 16
        (B) TYPE:   nucleic acid
        (C) STRANDEDNESS: single
        (D) TOPOLOGY:   linear (xi) SEQUENCE DESCRIPTION: SEQ ID NO: 4:

```
AATATCGCCC TGAGCA                                                      16
```

(2) INFORMATION FOR SEQ ID NO:5:

(i) SEQUENCE CHARACTERISTICS:
        (A) LENGTH: 188 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
Met Lys Asn Ile Ile Leu Ser Thr Leu Val Ile Thr Thr Ser Val Leu
1               5                   10                  15

Val Val Asn Val Ala Gln Ala Asp Thr Asn Ala Phe Ser Val Gly Tyr
            20                  25                  30

Ala Arg Tyr Ala Gln Ser Lys Val Gln Asp Phe Lys Asn Ile Arg Gly
        35                  40                  45

Val Asn Val Lys Tyr Arg Tyr Glu Asp Ser Pro Val Ser Phe Ile
    50                  55                  60

Ser Ser Leu Ser Tyr Leu Tyr Gly Asp Arg Gln Ala Ser Gly Ser Val
65                  70                  75                  80

Glu Pro Glu Gly Ile His Tyr His Asp Lys Phe Glu Val Lys Xaa Gly
                85                  90                  95

Ser Leu Met Val Gly Pro Ala Tyr Arg Leu Ser Asp Asn Phe Ser Leu
            100                 105                 110

Tyr Ala Leu Ala Gly Val Gly Thr Val Lys Ala Thr Phe Lys Glu His
        115                 120                 125

Ser Thr Gln Asp Gly Asp Ser Phe Ser Asn Lys Ile Ser Ser Arg Lys
    130                 135                 140

Thr Gly Phe Ala Trp Gly Ala Gly Val Gln Met Asn Pro Leu Glu Asn
145                 150                 155                 160

Ile Val Val Asp Val Gly Tyr Glu Gly Ser Asn Ile Ser Ser Thr Lys
                165                 170                 175

Ile Asn Gly Phe Asn Val Gly Val Gly Tyr Arg Phe
            180                 185
```